US009649172B2

(12) United States Patent
Blumenkranz et al.

(10) Patent No.: US 9,649,172 B2
(45) Date of Patent: *May 16, 2017

(54) OPTIC FIBER CONNECTION FOR A FORCE SENSING INSTRUMENT

(71) Applicant: Intuitive Surgical Operations, Inc., Sunnyvale, CA (US)

(72) Inventors: Stephen J. Blumenkranz, Los Altos Hills, CA (US); Gregory W. Dachs, II, San Mateo, CA (US); Ian E. McDowall, Woodside, CA (US); Christopher J. Hasser, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/141,691

(22) Filed: Apr. 28, 2016

(65) Prior Publication Data
US 2016/0235488 A1 Aug. 18, 2016

Related U.S. Application Data

(63) Continuation of application No. 14/714,580, filed on May 18, 2015, now Pat. No. 9,339,347, which is a (Continued)

(51) Int. Cl.
*G05B 15/00* (2006.01)
*G05B 19/00* (2006.01)
(Continued)

(52) U.S. Cl.
CPC ............. *A61B 34/20* (2016.02); *A61B 18/00* (2013.01); *A61B 34/30* (2016.02); *G01B 11/16* (2013.01);
(Continued)

(58) Field of Classification Search
CPC ........ A61B 19/2203; A61B 2019/2234; A61B 2019/464; A61B 2017/00477; G01L 1/242; G02B 6/264; Y10T 74/20335
(Continued)

(56) References Cited

U.S. PATENT DOCUMENTS 4,834,494 A 5/1989 DeMeritt et al.
4,836,637 A 6/1989 Poorman et al.
(Continued)

FOREIGN PATENT DOCUMENTS

FR 2693397 A1 1/1994
WO WO-2005039835 A1 5/2005
(Continued)

OTHER PUBLICATIONS

PCT/US10/28391 International Search Report and Written Opinion of the International Searching Authority, mailed Sep. 27, 2010, 16 pages.
(Continued)

Primary Examiner — Jaime Figueroa

(57) ABSTRACT

In one embodiment, a surgical instrument includes a housing linkable with a manipulator arm of a robotic surgical system, a shaft operably coupled to the housing, a force transducer on a distal end of the shaft, and a plurality of fiber optic strain gauges on the force transducer. In one example, the plurality of strain gauges are operably coupled to a fiber optic splitter or an arrayed waveguide grating (AWG) multiplexer. A fiber optic connector is operably coupled to the fiber optic splitter or the AWG multiplexer. A wrist joint is operably coupled to a distal end of the force transducer, and an end effector is operably coupled to the wrist joint. In another embodiment, a robotic surgical manipulator includes a base link operably coupled to a distal end of a manipulator positioning system, and a distal link movably
(Continued)

coupled to the base link, wherein the distal link includes an instrument interface and a fiber optic connector optically linkable to a surgical instrument. A method of passing data between an instrument and a manipulator via optical connectors is also provided.

9 Claims, 18 Drawing Sheets

Related U.S. Application Data continuation of application No. 13/892,223, filed on May 10, 2013, now Pat. No. 9,055,962, which is a continuation of application No. 12/415,795, filed on Mar. 31, 2009, now Pat. No. 8,463,439.

(51) Int. Cl.
| | |
|---|---|
| *A61B 34/20* | (2016.01) |
| *A61B 34/30* | (2016.01) |
| *G01L 1/24* | (2006.01) |
| *G02B 6/26* | (2006.01) |
| *A61B 18/00* | (2006.01) |
| *G01B 11/16* | (2006.01) |
| *G02B 6/12* | (2006.01) |
| *G02B 6/32* | (2006.01) |
| *A61B 90/00* | (2016.01) |
| *A61B 17/00* | (2006.01) |

(52) U.S. Cl.
CPC .......... *G01L 1/242* (2013.01); *G02B 6/12019* (2013.01); *G02B 6/264* (2013.01); *G02B 6/32* (2013.01); *A61B 2017/00477* (2013.01); *A61B 2034/2061* (2016.02); *A61B 2034/305* (2016.02); *A61B 2090/064* (2016.02); *A61B 2562/0266* (2013.01); *Y10T 74/20335* (2015.01)

(58) Field of Classification Search
USPC .......... 700/245, 258; 74/490.06; 385/33, 39, 385/43, 46, 74; 606/130; 901/29, 30, 33, 901/34, 46, 47
See application file for complete search history.

(56) References Cited

U.S. PATENT DOCUMENTS

| | | | |
|---|---|---|---|
| 4,889,399 A | 12/1989 | Mariani et al. | |
| 4,898,450 A | 2/1990 | Jannson et al. | |
| 4,913,510 A | 4/1990 | Lynch et al. | |
| 4,953,938 A | 9/1990 | Buhrer et al. | |
| 5,257,332 A | 10/1993 | Pimpinella | |
| 5,631,973 A | 5/1997 | Green | |
| 5,807,377 A | 9/1998 | Madhani et al. | |
| 5,838,437 A | 11/1998 | Miller et al. | |
| 5,996,376 A | 12/1999 | Johnson et al. | |
| RE36,592 E | 2/2000 | Giebel et al. | |
| 6,221,007 B1 | 4/2001 | Green | |
| 6,246,200 B1 | 6/2001 | Blumenkranz et al. | |
| 6,256,090 B1 | 7/2001 | Chen et al. | |
| 6,263,133 B1 | 7/2001 | Hamm | |
| 6,331,181 B1 | 12/2001 | Tierney et al. | |
| 6,371,952 B1 | 4/2002 | Madhani et al. | |
| 6,374,012 B1 | 4/2002 | Bergmann et al. | |
| 6,411,755 B1 | 6/2002 | Erdogan | |
| 6,493,489 B2 | 12/2002 | Mertz et al. | |
| 6,574,355 B2 | 6/2003 | Green | |
| 6,632,025 B2 | 10/2003 | Ukrainczyk | |
| 6,655,850 B2 | 12/2003 | Mann et al. | |
| 6,676,684 B1 | 1/2004 | Morley et al. | |
| 6,736,547 B2 | 5/2004 | Stevens et al. | |
| 6,770,081 B1 | 8/2004 | Cooper et al. | |
| 6,783,524 B2 | 8/2004 | Anderson et al. | |
| 6,817,974 B2 | 11/2004 | Cooper et al. | |
| 6,865,332 B1 | 3/2005 | Saravanos et al. | |
| 6,866,671 B2 | 3/2005 | Tierney et al. | |
| 6,879,880 B2 | 4/2005 | Nowlin et al. | |
| 6,902,560 B1 | 6/2005 | Morley et al. | |
| 6,936,042 B2 | 8/2005 | Wallace et al. | |
| 7,031,567 B2 | 4/2006 | Grinderslev et al. | |
| 7,200,300 B2 | 4/2007 | Barefoot et al. | |
| 7,218,828 B2 | 5/2007 | Feustel et al. | |
| 7,258,495 B1 | 8/2007 | Hughes, Jr. et al. | |
| 7,350,981 B2 | 4/2008 | Durrant et al. | |
| 7,460,750 B2 | 12/2008 | Durrant et al. | |
| 7,463,913 B2 | 12/2008 | Nagashima | |
| 7,666,191 B2 | 2/2010 | Orban, III et al. | |
| 7,699,855 B2 | 4/2010 | Anderson et al. | |
| 7,727,244 B2 | 6/2010 | Orban, III et al. | |
| 7,752,920 B2 | 7/2010 | Larkin et al. | |
| 8,157,789 B2 * | 4/2012 | Leo ...................... | A61B 5/6885 600/182 |
| 8,182,470 B2 | 5/2012 | Devengenzo et al. | |
| 8,375,808 B2 | 2/2013 | Blumenkranz et al. | |
| 8,385,738 B2 * | 2/2013 | Mahlab .............. | H04Q 11/0005 398/49 |
| 8,463,439 B2 | 6/2013 | Blumenkranz et al. | |
| 8,496,647 B2 | 7/2013 | Blumenkranz et al. | |
| 8,622,935 B1 | 1/2014 | Leo | |
| 8,628,518 B2 * | 1/2014 | Blumenkranz ........ | A61B 19/20 606/1 |
| 9,055,962 B2 | 6/2015 | Blumenkranz et al. | |
| 2004/0067003 A1 | 4/2004 | Chliaguine et al. | |
| 2005/0105902 A1 | 5/2005 | Alavie et al. | |
| 2005/0148997 A1 | 7/2005 | Valley et al. | |
| 2005/0151975 A1 * | 7/2005 | Melnyk ................. | G01B 11/18 356/480 |
| 2005/0200324 A1 | 9/2005 | Guthart et al. | |
| 2007/0058897 A1 | 3/2007 | Yong et al. | |
| 2007/0060847 A1 | 3/2007 | Leo et al. | |
| 2007/0065077 A1 | 3/2007 | Childers et al. | |
| 2007/0151390 A1 | 7/2007 | Blumenkranz et al. | |
| 2007/0156019 A1 | 7/2007 | Larkin et al. | |
| 2007/0165238 A1 | 7/2007 | Boyd | |
| 2007/0213743 A1 | 9/2007 | McGuckin, Jr. | |
| 2007/0265503 A1 | 11/2007 | Schlesinger et al. | |
| 2008/0285909 A1 | 11/2008 | Younge et al. | |
| 2009/0093867 A1 | 4/2009 | Schwarz et al. | |
| 2009/0103927 A1 * | 4/2009 | Cunningham ..... | H04B 10/6971 398/139 |
| 2009/0123111 A1 | 5/2009 | Udd | |
| 2009/0317083 A1 * | 12/2009 | Prat Goma .......... | H04J 14/0201 398/68 |
| 2010/0250000 A1 * | 9/2010 | Blumenkranz ........ | A61B 34/30 700/258 |
| 2011/0087112 A1 | 4/2011 | Leo et al. | |
| 2011/0103748 A1 * | 5/2011 | Ott ....................... | G02B 6/3835 385/78 |
| 2013/0016360 A1 | 1/2013 | Ensher et al. | |
| 2015/0250548 A1 | 9/2015 | Blumenkranz et al. | |

FOREIGN PATENT DOCUMENTS

| | | |
|---|---|---|
| WO | WO-2007047506 A2 | 4/2007 |
| WO | WO-2009004616 A2 | 1/2009 |

OTHER PUBLICATIONS

PCT/US10/28391 Partial International Search Report and Invitation to Pay Additional Fees, mailed Jul. 1, 2010, 5 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

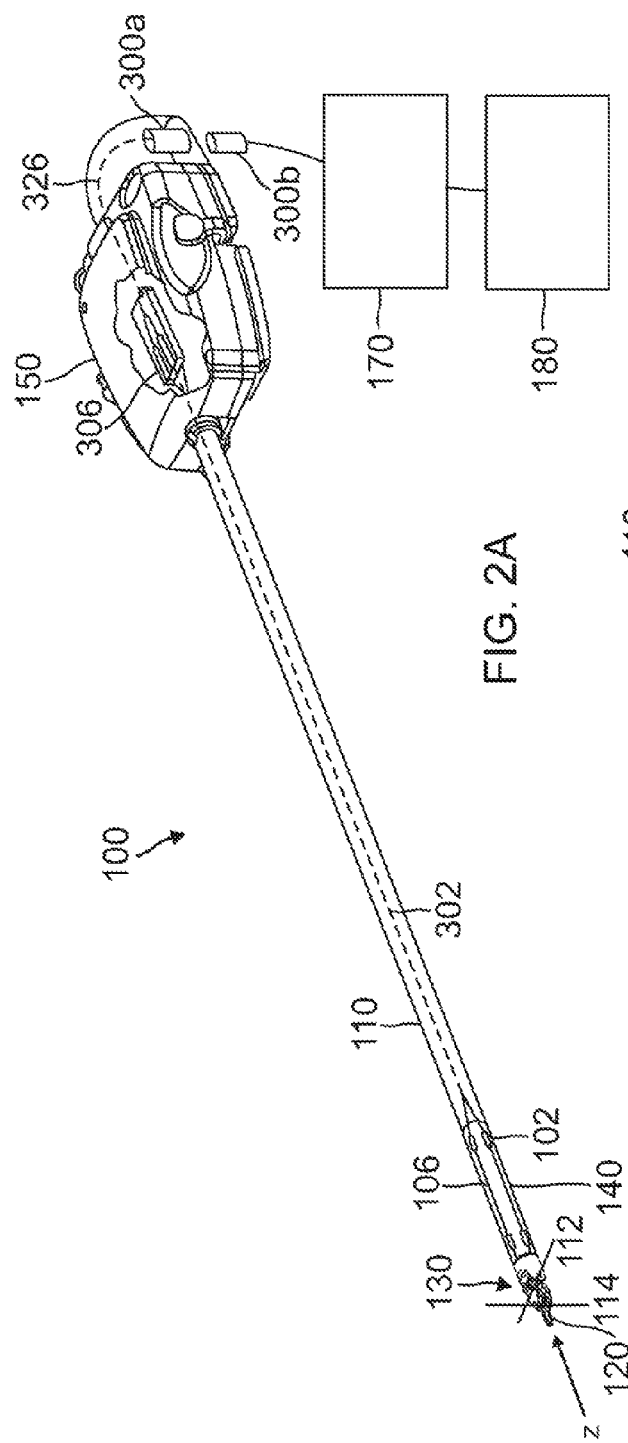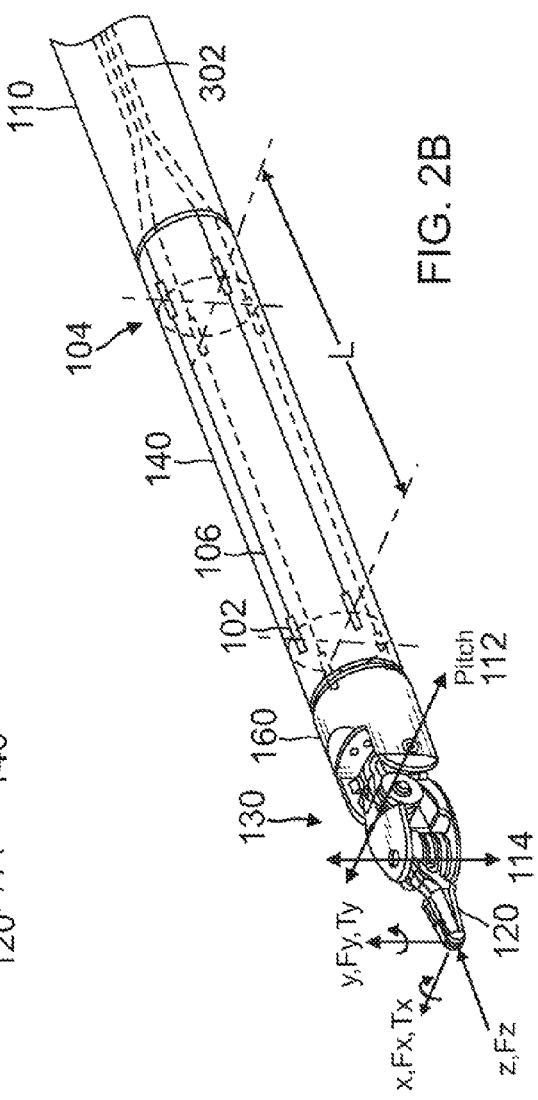
FIG. 2A
FIG. 2B

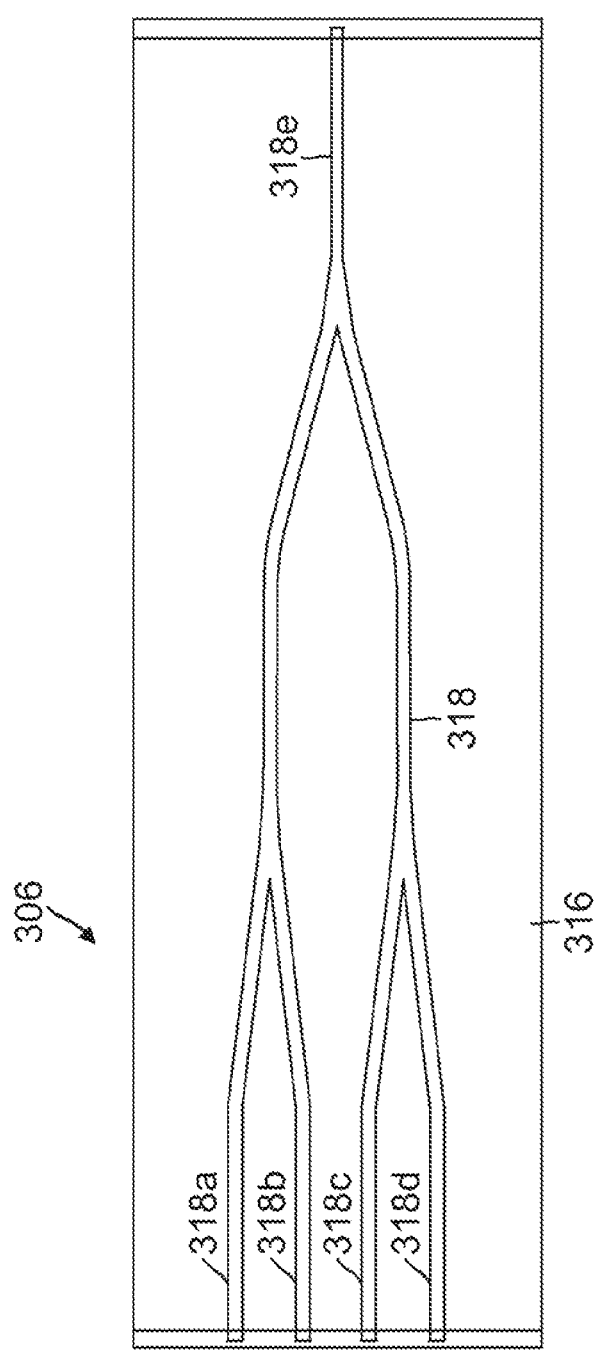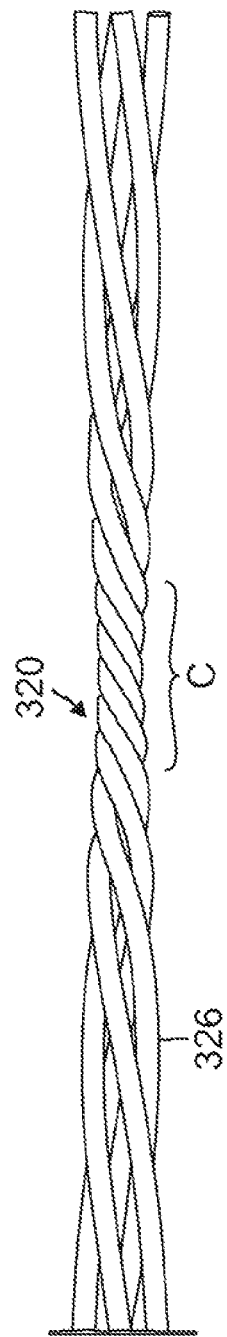

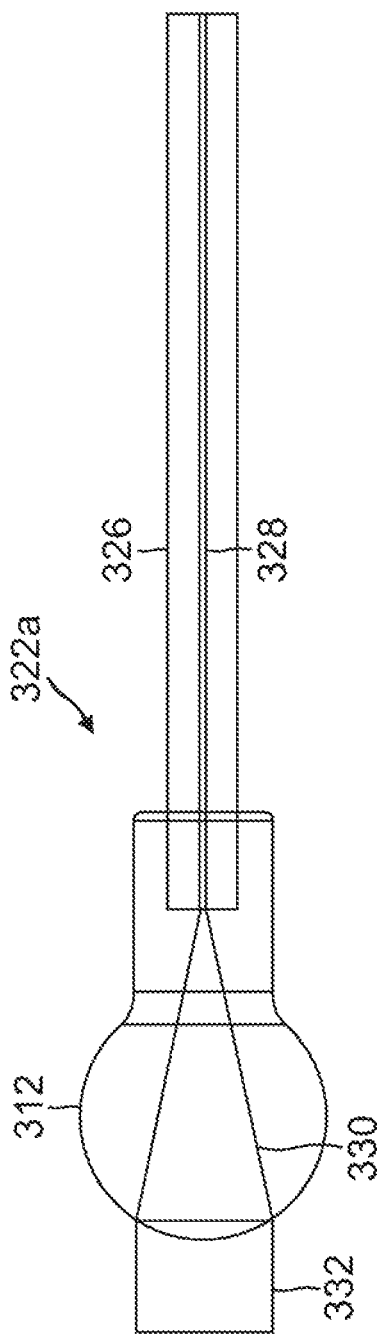
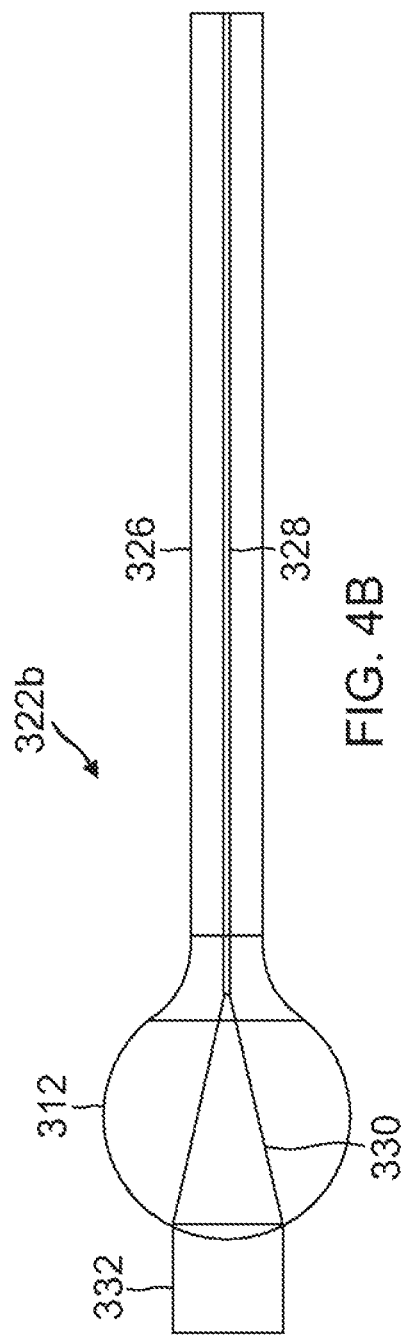
FIG. 4A
FIG. 4B

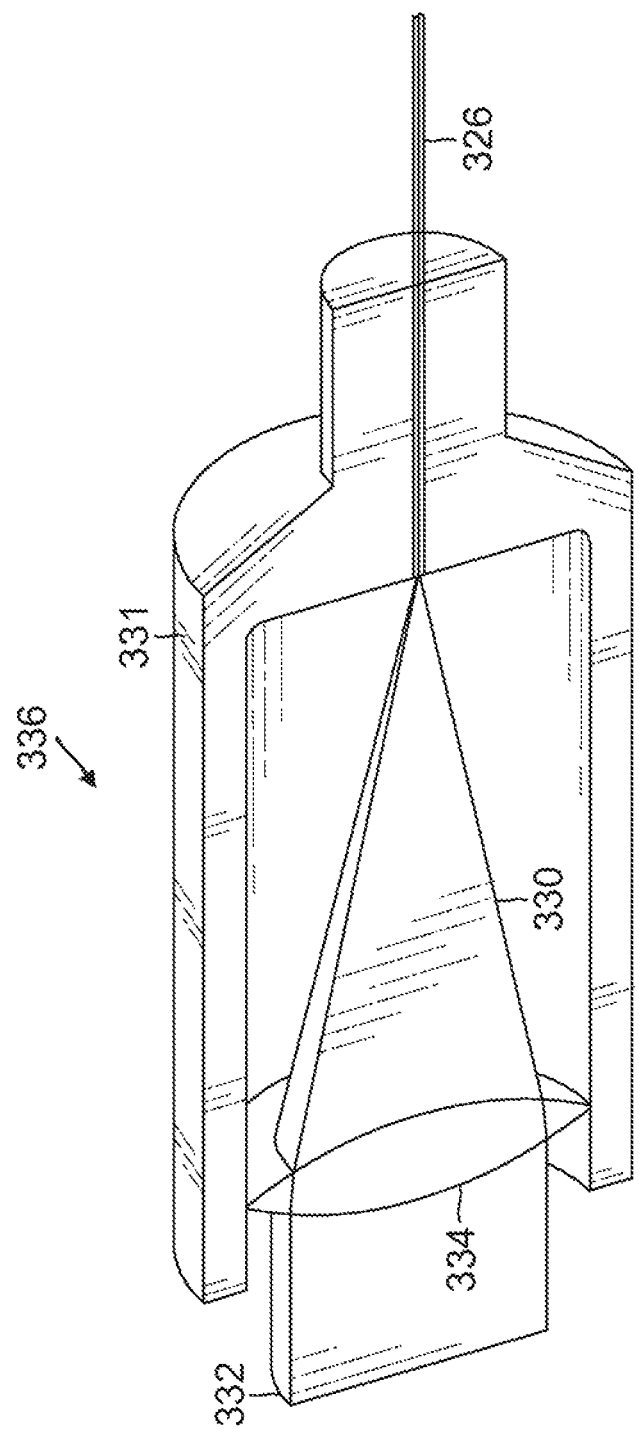

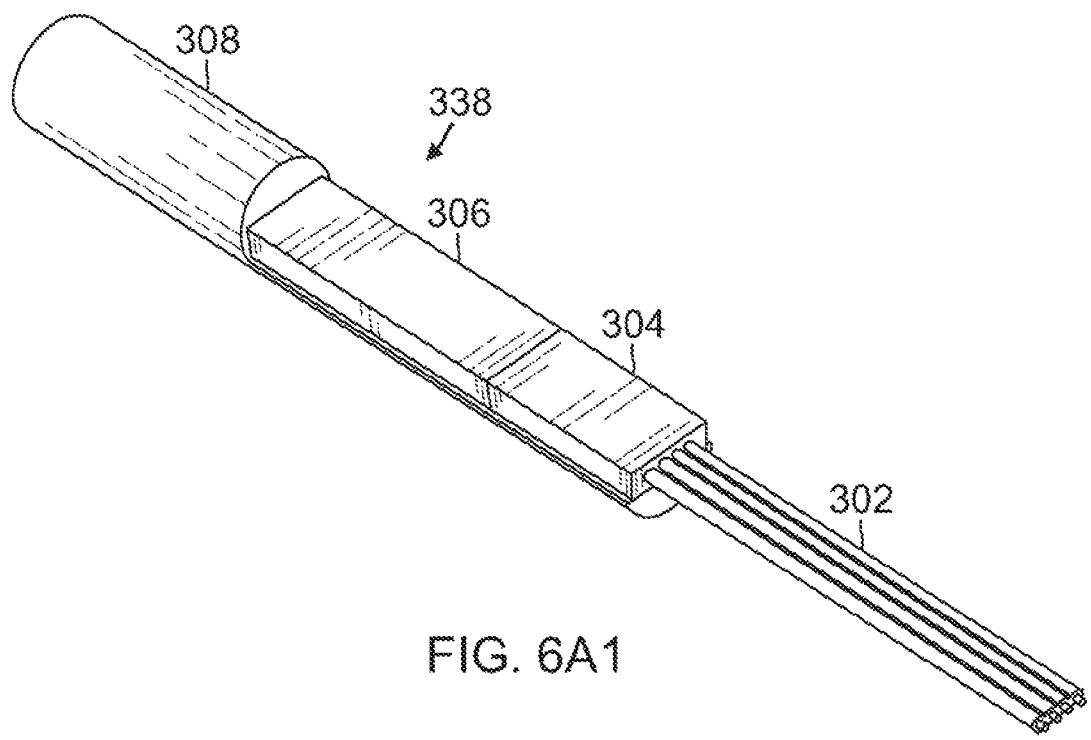
FIG. 6A1
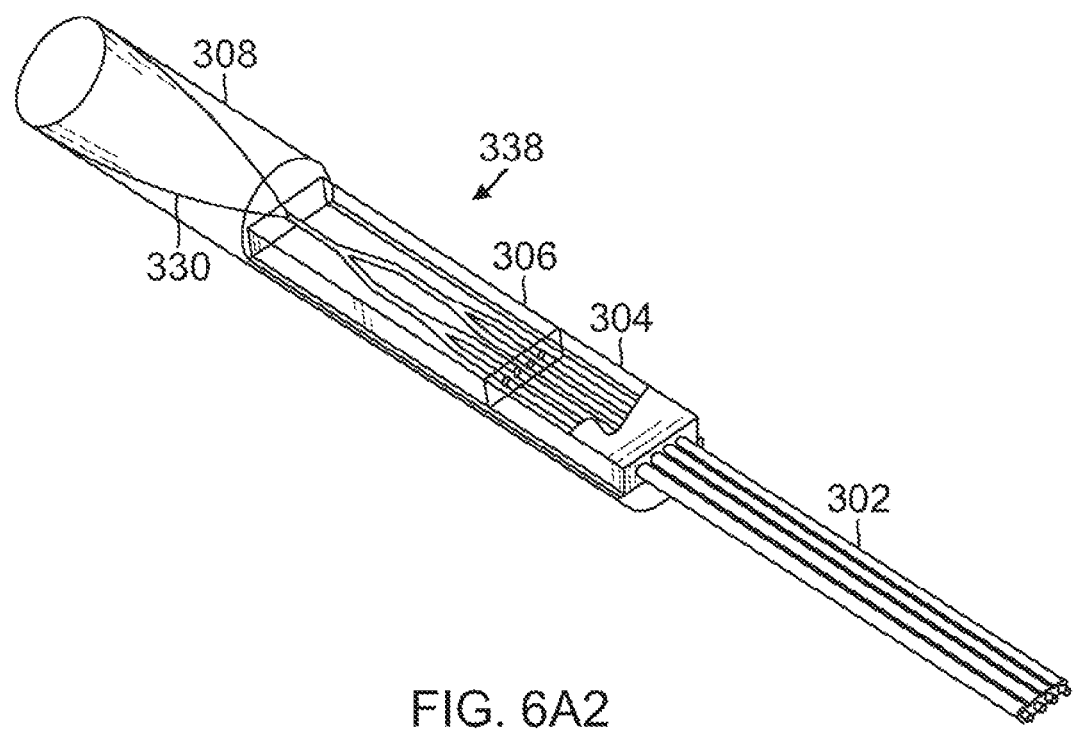
FIG. 6A2

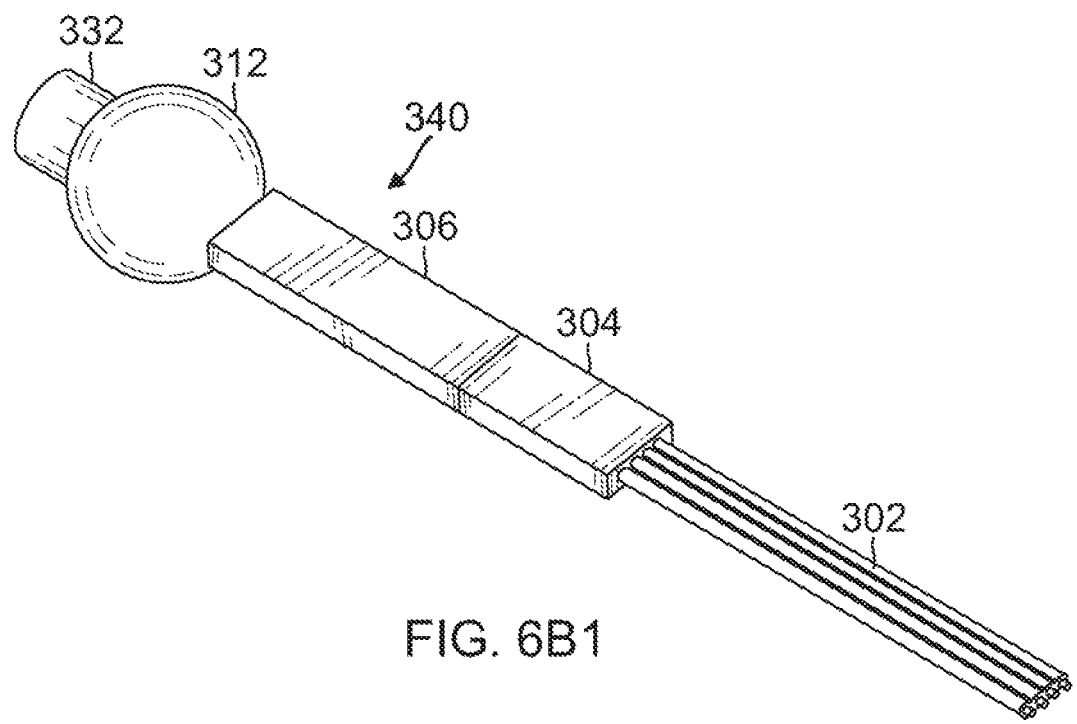
FIG. 6B1
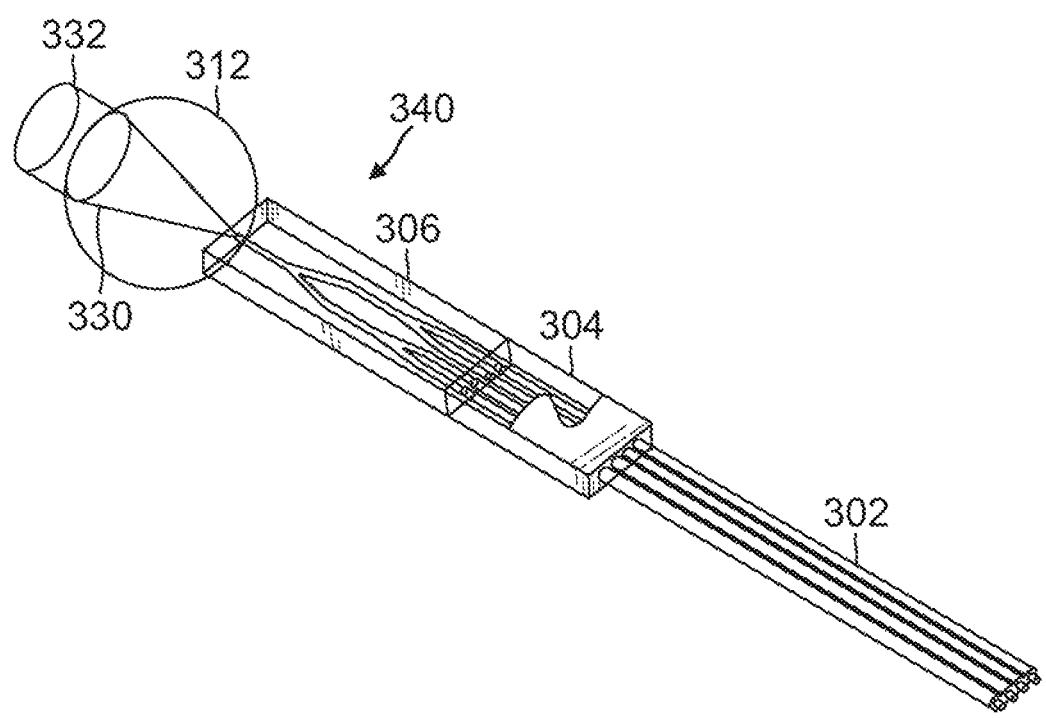
FIG. 6B2

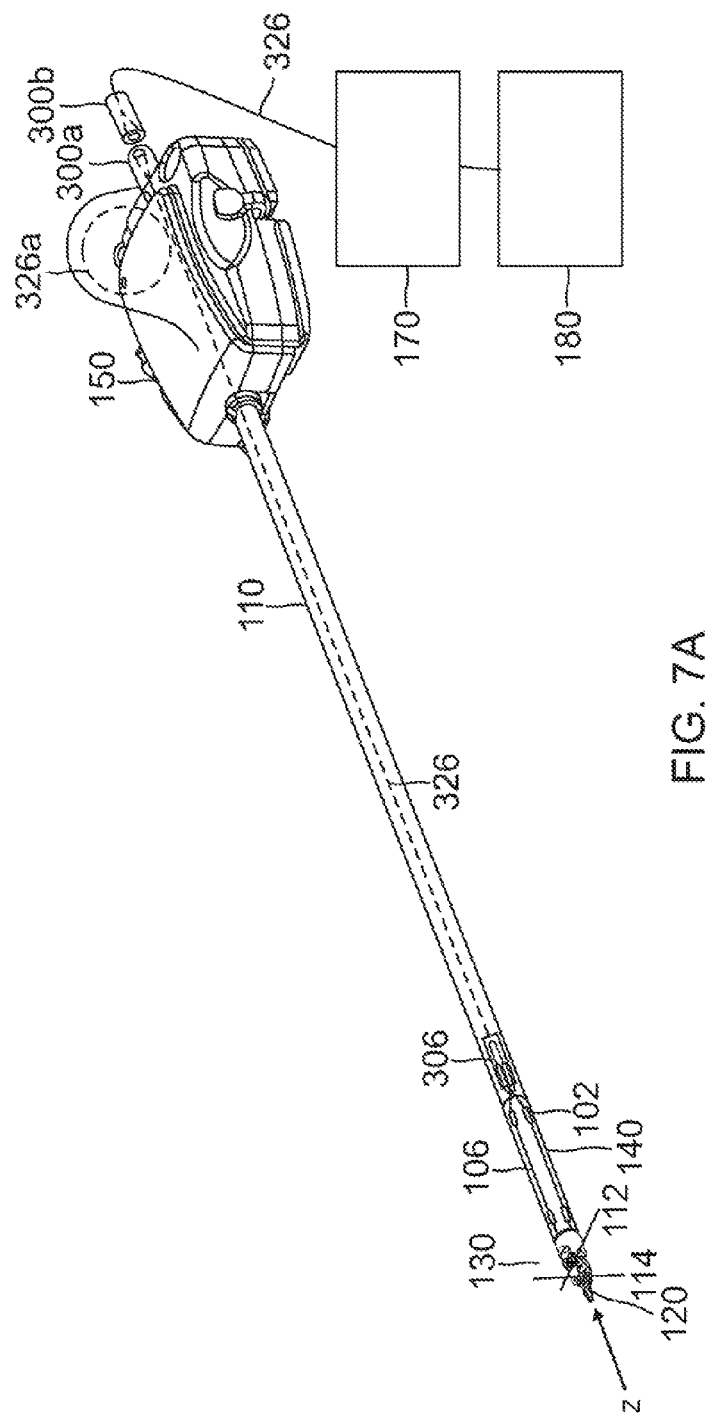
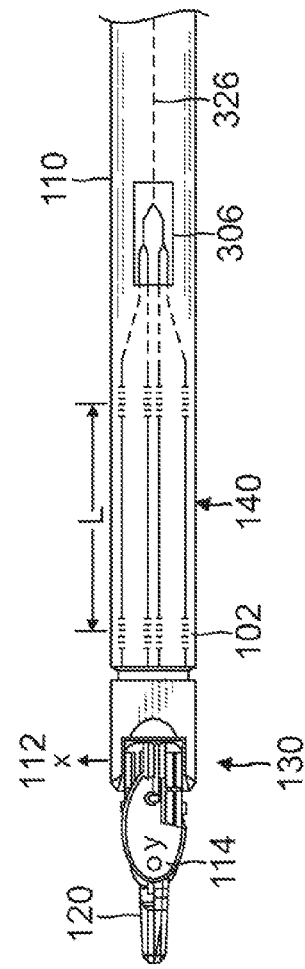
FIG. 7A
FIG. 7B

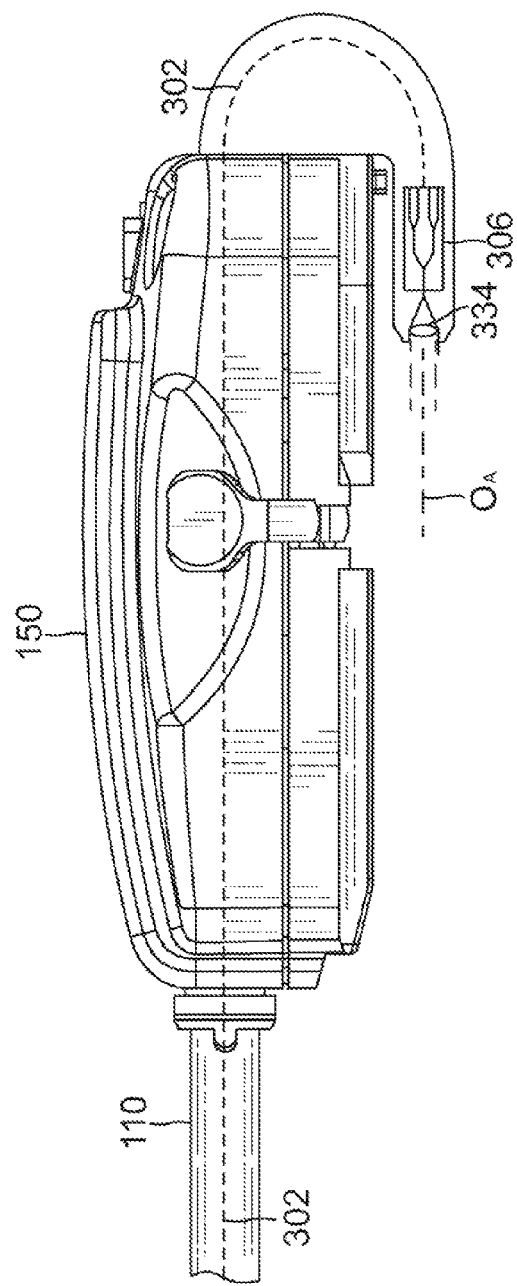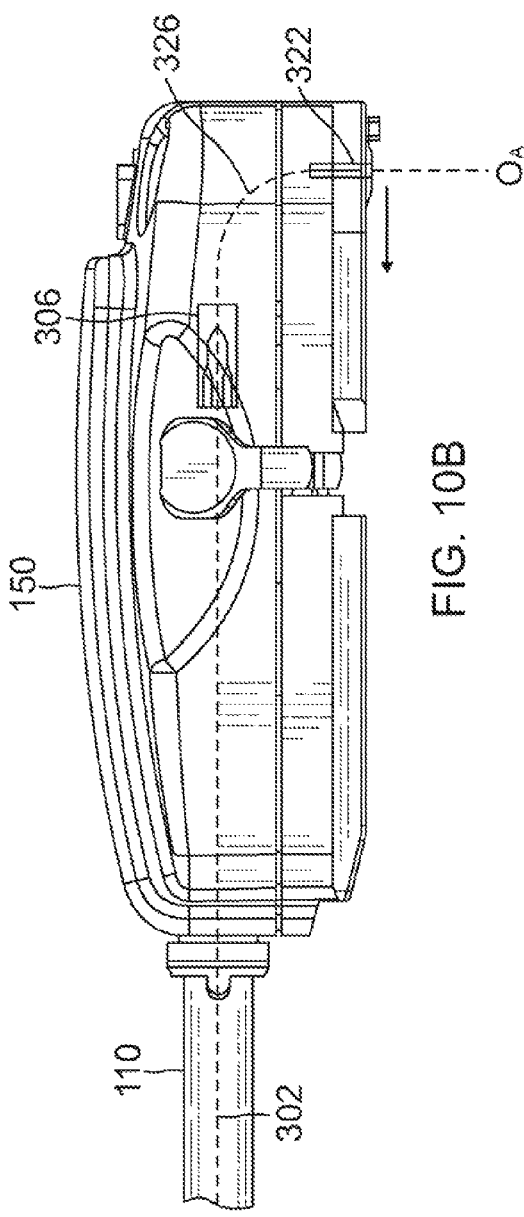
FIG. 10A
FIG. 10B

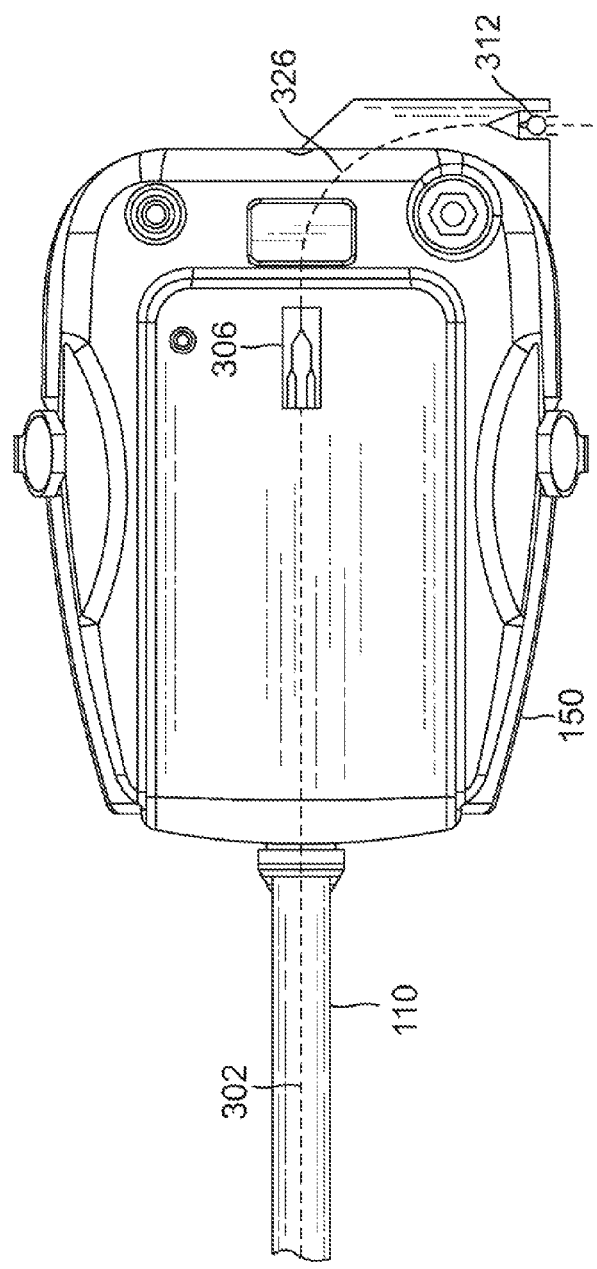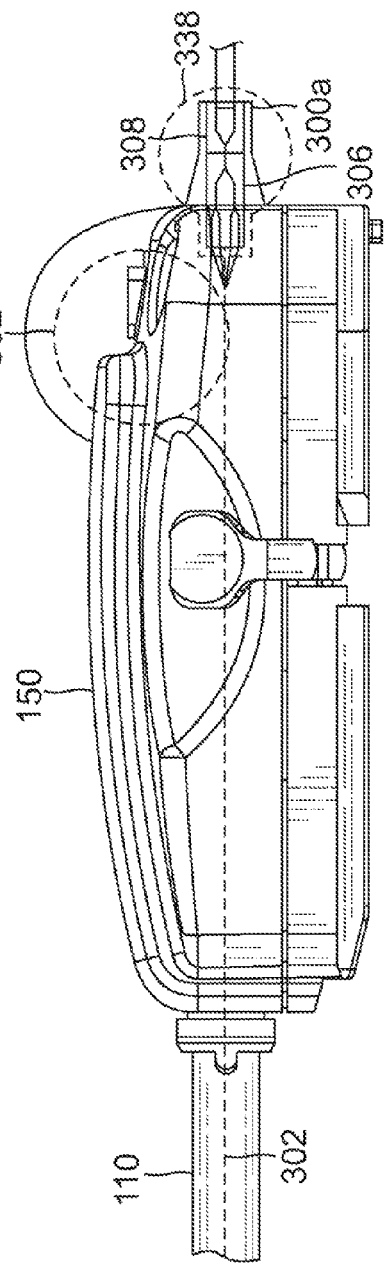
FIG. 10C
FIG. 10D

OPTIC FIBER CONNECTION FOR A FORCE SENSING INSTRUMENT

CROSS-REFERENCE TO RELATED APPLICATIONS AND PATENTS

This application is a continuation application of U.S. application Ser. No. 14/714,580 (filed May 18, 2015), which is a continuation application of U.S. application Ser. No. 13/892,223 (filed May 10, 2013, now U.S. Pat. No. 9,055,962, issued Jun. 16, 2015), which is a continuation application of U.S. application Ser. No. 12/415,795 (filed Mar. 31, 2009, now U.S. Pat. No. 8,463,439, issued Jun. 11, 2013), which is related to U.S. application Ser. No. 11/537,241, filed Sep. 29, 2006, which claimed priority to U.S. Provisional Application No. 60/755,108 filed Dec. 30, 2005, the full disclosures of which are incorporated by reference herein for all purposes.

This application is further related to U.S. Provisional Application 60/755,157 filed Dec. 30, 2005, U.S. application Ser. No. 11/958,772 filed Dec. 18, 2007, U.S. application Ser. No. 11/864,974 filed Sep. 29, 2007, U.S. application Ser. No. 11/553,303 filed Oct. 26, 2006, U.S. application Ser. No. 11/093,372 filed Mar. 30, 2005, and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to apparatus and methods for data communication related to sensing forces applied to a surgical instrument and/or a surgical robotic manipulator.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves inserted through incisions into a body cavity, such as the patient's abdomen. Depending on the surgical procedure, there are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, or dissecting, cauterizing or coagulating tissue.

This method of performing telerobotic surgery through remote manipulation has created many new challenges. One such challenge is providing the surgeon with the ability to accurately "feel" the tissue that is being manipulated by the surgical instrument via the robotic manipulator. The surgeon must rely on indications of the forces applied by the instruments or sutures. It is desirable to sense the forces applied to the tip of the instrument, such as an end effector (e.g., jaws, grasper, blades, etc.) of robotic endoscopic surgical instruments, in order to feed the forces back to the surgeon user through the system hand controls or by other means such as visual display or audible tone.

A surgeon may employ a large number of different surgical instruments/tools during a procedure. Some of the surgical instruments may include fiber optic force sensors on multiple optic fibers, and it is desirable to make a reliable and robust optical connection with the surgical system when the instrument is electrically and mechanically mounted to the robotic manipulator. It is also desirable to combine the signals from multiple sensor fibers into one fiber to improve optical connection.

What is needed, therefore, are improved telerobotic systems, apparatus, and methods for remotely controlling surgical instruments at a surgical site on/in a patient. In particular, these systems, apparatus, and methods should be configured to provide accurate feedback of forces to the surgeon to improve user awareness and control of the instruments and manipulator.

SUMMARY

The present invention provides a surgical instrument, manipulator, and method for improving force feedback to and sensing by a surgeon performing telerobotic surgery. In particular, a surgical instrument comprises a housing including an optic fiber connector that is optically linkable with a manipulator arm of a robotic surgical system, a shaft operably coupled to the housing, and a plurality of strain gauges on a force transducer on a distal end of the shaft, the plurality of strain gauges operably coupled to the optic fiber connector. The instrument further includes a wrist joint operably coupled to the distal end of the force transducer, and an end effector operably coupled to the wrist joint.

In another embodiment, a robotic surgical manipulator comprises a manipulator arm, including a base link operably coupled to a manipulator positioning arm and a distal link of the manipulator arm, movably coupled to the base link. The distal link includes an instrument interface and an optic fiber connector optically linkable to a surgical instrument.

In yet another embodiment, a method of force sensing at the tip of a robotic surgical instrument comprises providing a robotic surgical manipulator including a first optic fiber connector, and mounting a removable surgical instrument on the robotic surgical manipulator, the surgical instrument including a plurality of strain gauges on a force transducer on a distal end of a shaft and a second optic fiber connector that is optically linkable with the first optic fiber connector of the manipulator. The method further includes passing data from the plurality of strain gauges to the first optic fiber connector through the second optic fiber connector.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 2A illustrates a perspective view of a force sensing robotic surgical instrument, and FIG. 2B illustrates an enlarged view of a distal end of the surgical instrument in accordance with an embodiment of the present invention.

FIGS. 3A and 3B show orthographic views of planar lightwave circuit (PLC) and fused biconic taper (FBT) fiber optic splitters, respectively.

FIGS. 4A and 4B are longitudinal cross-section views of lensed optical fiber, which are components of some embodiments of the present invention.

FIG. 5 illustrates a type of fiber collimator comprising a housing, an aspheric lens and an optic fiber in focal alignment, that may be used as an expanded beam fiber optic connector in embodiments of the present invention.

FIGS. 6A1 and 6A2 illustrate a perspective view and a partial cutaway perspective view, respectively, of a PLC fiber optic splitter operably coupled to a gradient index (GRIN) lens collimator.

FIGS. 6B1 and 6B2 illustrate a perspective view and a partial cutaway perspective view, respectively, of a PLC fiber optic splitter operably coupled to a ball lens collimator.

FIG. 7A illustrates a surgical instrument with a force transducer comprising a plurality of fiber Bragg grating strain gauges operably coupled to a PLC fiber optic splitter, and FIG. 7B illustrates an enlarged view of a distal end of the surgical instrument with the force transducer.

FIGS. 10A-10D show orthographic views of an instrument rear housing including a fiber optic ribbon cable, a PLC fiber optic splitter, a strain relief loop of optical fiber or ribbon cable and an expanded beam optic fiber connector in accordance with an embodiment of the present invention.

Figure 1A:
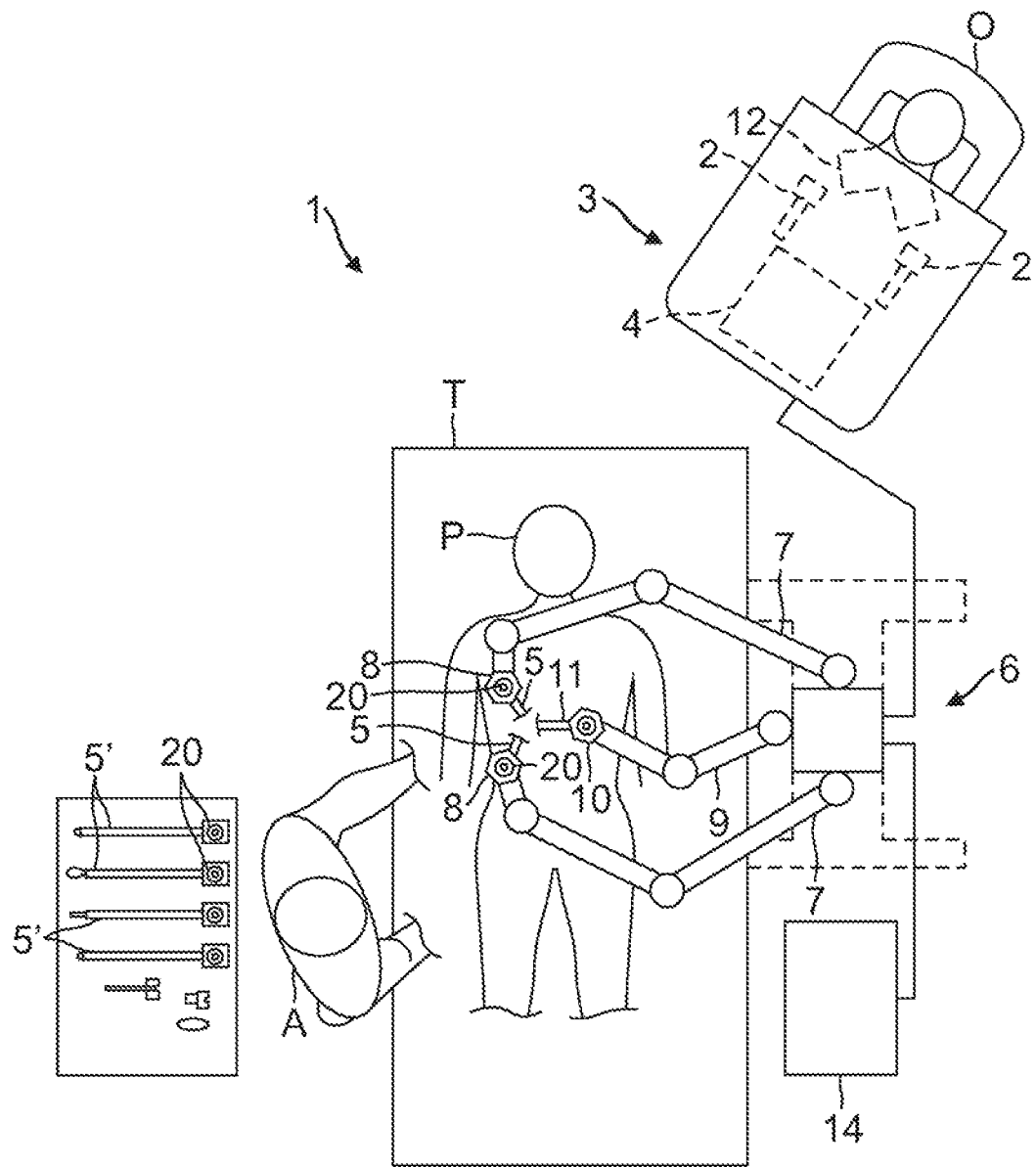
FIG. 1A is a plan view of a robotic surgical environment in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces while performing robotically-assisted surgical procedures on a patient, particularly including open surgical procedures, neurosurgical procedures, and minimally invasive endoscopic procedures, such as laparoscopy, arthroscopy, thoracoscopy, and the like. The system and method of the present invention are particularly useful as part of a telerobotic surgical system that allows the surgeon to manipulate the surgical instruments through a servomechanism from a location remote from the patient. To that end, the combined manipulator apparatus or slave and the attached surgical instrument of the present invention will usually be driven by a master having equivalent degrees of freedom (e.g., 3 degrees of freedom for position, 3 degrees of freedom for orientation plus grip) to form a telepresence system with force reflection or display. A description of a suitable slave-master system can be found in U.S. Pat. No. 6,574,355, the complete disclosure of which is incorporated herein by reference for all purposes.

A robotic system of the present invention generally includes one or more surgical manipulator assemblies mounted to or near an operating table and a master control assembly for allowing a surgeon to view the surgical site and to control the manipulator assemblies. The system will also include one or more viewing scope assemblies and a plurality of surgical instruments adapted for being removably coupled to the manipulator assemblies (discussed in more detail below). The robotic system includes at least two manipulator assemblies and preferably at least three manipulator assemblies. As discussed in detail below, one of the assemblies will typically operate a viewing scope assembly (e.g., in endoscopic procedures) for viewing the surgical site, while the other manipulator assemblies operate surgical instruments for performing various procedures on a patient.

The control assembly may be located at a surgeon's console which is usually located in the same room as the operating table so that the surgeon may speak to his/her assistant(s) and directly monitor the operating procedure. However, it should be understood that the surgeon can be located in a different room or a completely different building from the patient. The master control assembly generally includes a support, a monitor for displaying an image of the surgical site to the surgeon, and one or more master(s) for controlling the manipulator assemblies. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the associated manipulator with surgical instrument assemblies to provide part of the surgeon telepresence, the perception that the surgeon is immediately adjacent to and immersed in the surgical site, and intuitiveness, the perception that the master(s) are integral with the instruments so that the surgeon has a strong sense of directly and intuitively controlling instruments as if they are part of his or her hands. Position, force, and tactile feedback sensors may also be employed on instrument assemblies to transmit signals that may be used to represent position, force, and tactile sensations from the surgical instrument back to the surgeon's hands as he/she operates the telerobotic system. One suitable system and method for providing telepresence to the operator is described in U.S. Pat. No. 6,574,355, which has previously been incorporated herein by reference.

The monitor will be suitably coupled to the viewing scope assembly such that an image of the surgical site is provided adjacent the surgeon's hands on the surgeon console. Preferably, the monitor will display an image on a display that is oriented so that the surgeon feels that he or she is actually looking directly down onto the operating site. To that end, an image of the surgical instrument appears to be located substantially where the operator's hands are located and oriented substantially as the operator would expect it to be based on his/her hand positions. In addition, the real-time image is preferably a stereo image such that the operator can manipulate the end effector and the hand control as if viewing the workspace in substantially true presence. By true presence, it is meant that which the operator would see if directly viewing and physically manipulating the surgical instruments. Thus, a controller transforms the coordinates of the surgical instruments to a perceived orientation so that the stereo image is the image that one would see if, for example, the camera or endoscope was located directly behind the surgical instruments. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

A servo control is provided for transferring the mechanical motion of masters to the manipulator assemblies. The servo control may provide force and torque feedback from the surgical instruments to the hand-operated masters. In addition, the servo control may include a safety monitoring controller to safely halt system operation, or at least inhibit all robot motion, in response to recognized undesirable conditions (e.g., exertion of excessive force on the patient, mismatched encoder readings, etc.).

Figure 1B:
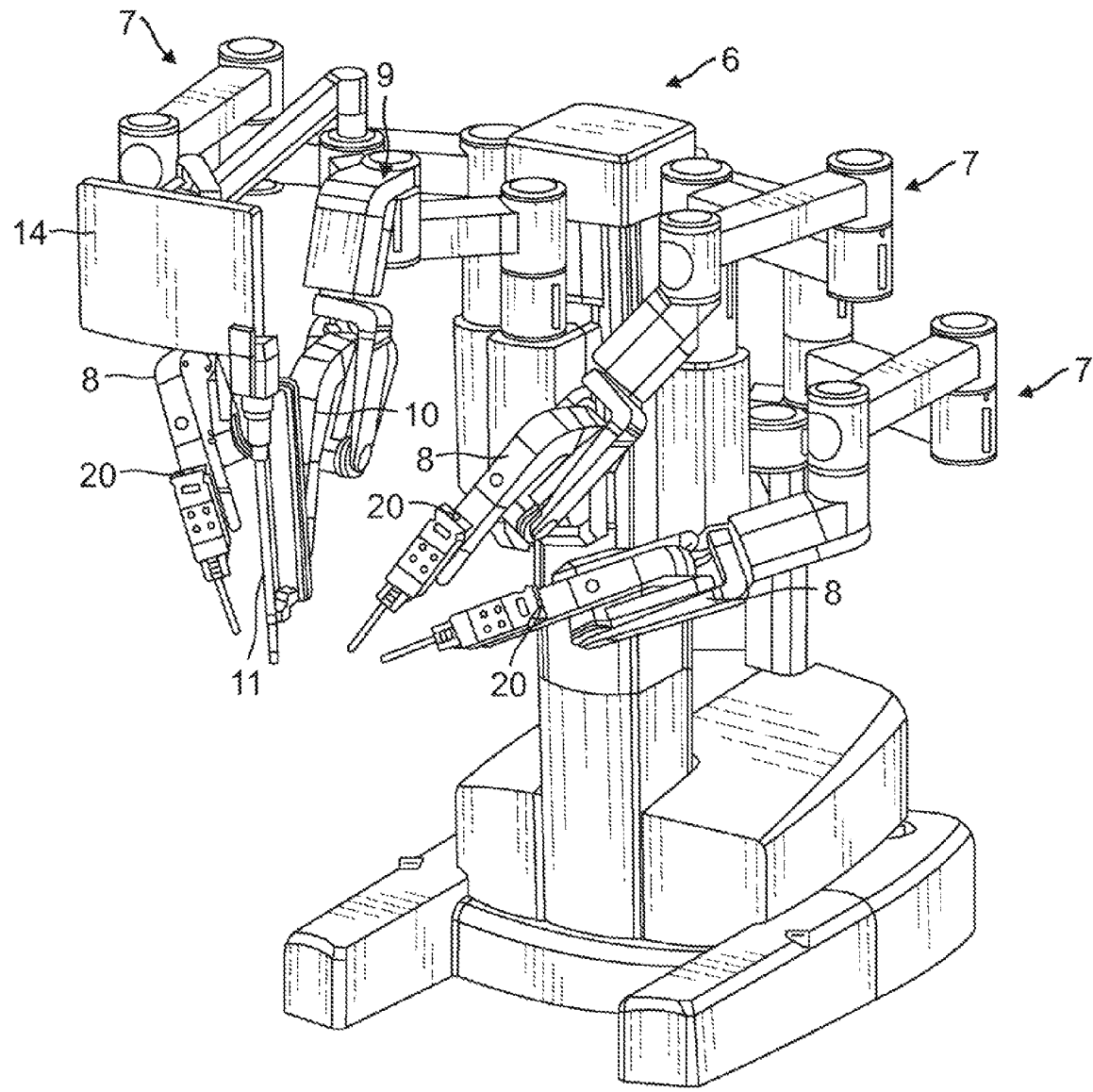
FIG. 1B illustrates a perspective view of an embodiment of a robotic surgical manipulator system.

Referring now to the drawings in detail, wherein like numerals indicate like elements, FIGS. 1A-1B illustrate components of a robotic surgical system 1 for performing minimally invasive robotic surgery in accordance with an embodiment of the present invention. System 1 is similar to that described in more detail in U.S. Pat. No. 6,246,200, the full disclosure of which is incorporated herein by reference.

A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servo-mechanical movement of the instruments via a robotic patient-side manipulator system 6 (a cart-based system in this example) including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software to implement some or all of the methods described herein. While processor 4 is shown as a single block in the simplified schematic of FIG. 1A, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator system 6 includes at least four robotic manipulator assemblies. Three setup linkages 7 (mounted at the sides of the cart in this example) support and position manipulators 8 with linkages 7 in general supporting a base link 30 of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "setup arm".

Assistant A assists in pre-positioning manipulators 8 and 10 relative to patient P using setup linkage arms 7 and 9, respectively; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during setup of patient-side manipulator system 6, and typically remain in a fixed configuration during at least a portion of a surgical procedure. Manipulators 8, 10 each comprise a driven linkage which is actively articulated under the direction of the surgeon at console 3. Although one or more of the joints of the setup arm may optionally be driven and robotically controlled, at least some of the setup arm joints may be configured for manual positioning by assistant A.

In one example, the image of the internal surgical site is shown to operator O by a stereoscopic display 12 in surgeon's console 3. The internal surgical site is simultaneously shown to assistant A by an assistance display 14.

Some of the manipulators may include a telescopic insertion axis (e.g., telescopic insertion axis 60 of FIGS. 11, 12A and 13A), although in other embodiments, all of the manipulators may include a telescopic insertion axis. Telescopic insertion axis 60 allows for movement of a mounted instrument (e.g., instrument 5 of FIG. 1A or instrument 100 of FIG. 13A-13B), via three operably coupled links, in one example, with improved stiffness and strength compared to previous designs, a larger range of motion, and improved dynamic performance and visibility proximate the surgical field for system users (in addition to other advantages), as is described in greater detail in U.S. application Ser. No. 11/613,800 filed Dec. 20, 2006, the full disclosure of which is incorporated by reference herein for all purposes.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Referring now to FIGS. 2A-13B in conjunction with FIGS. 1A-1B, an apparatus, system, and method for sensing and feedback of forces to the surgeon will be described with respect to using surgical instruments including strain gauges. It is noted that the below-described instruments are examples and various instruments that provide force signals may be modified within the scope of the present invention.

Figure 12A:
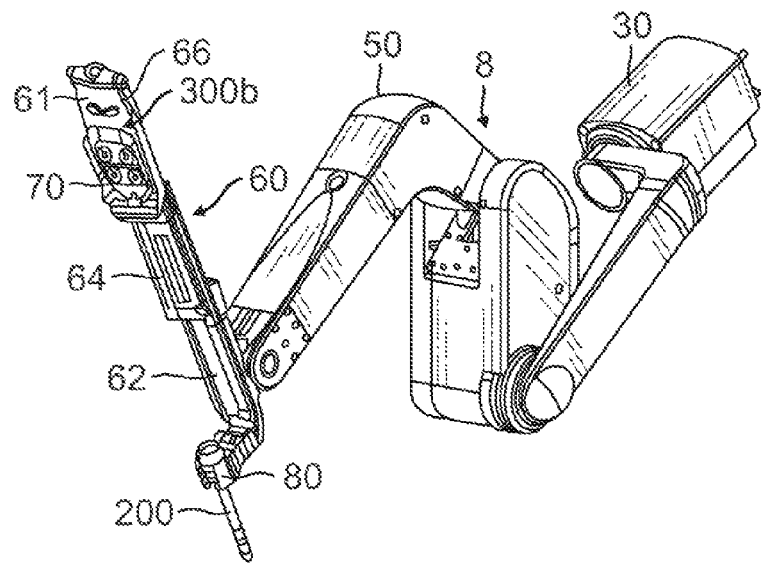
FIG. 12A is a perspective view of the manipulator of FIG. 11, including the optic fiber connector and including the coupling of a sterile adaptor to the instrument interface that allows for the use of the optic fiber connector, in accordance with an embodiment of the present invention.
Figure 12B:
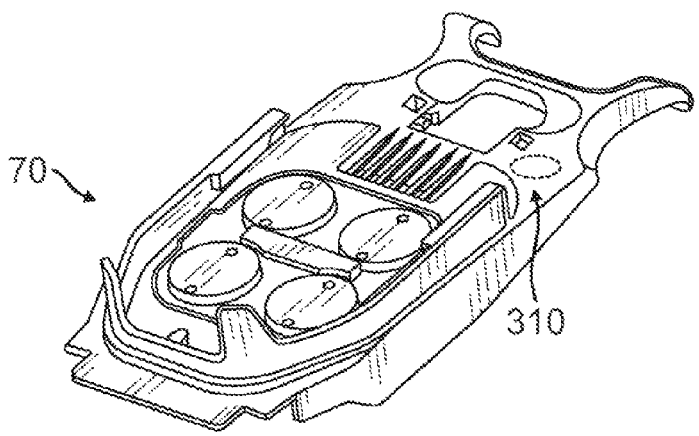
FIG. 12B is an enlarged view of the sterile adaptor.
Figure 12C:
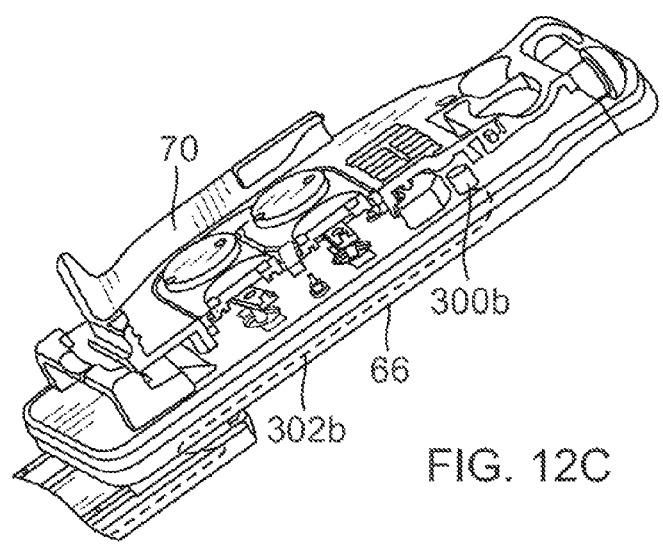
FIG. 12C is an enlarged sectional view of the sterile adaptor coupled to the distal link instrument interface in accordance with an embodiment of the present invention.

FIG. 2A shows a perspective view of a surgical instrument 100 that includes a shaft 110, a wrist 130 comprising joints for movement about axes 112 and 114, and an end portion 120 that may be used to manipulate a surgical tool (e.g., a needle) and/or contact the patient. The surgical instrument also includes a housing 150 that operably interfaces with a robotic manipulator arm, in one embodiment via a sterile adaptor interface (FIGS. 12A-12C). Housing 150 includes the motion inputs and wrist cable actuator mechanisms. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch about axis 112 and yaw about axis 114, which are parallel to the x- and y-axes respectively, and rotation about the z-axis as shown in FIG. 2B. These motions, as well as actuation of an end effector, are done via cables running through shaft 110 and housing 150 that transfer motion from the manipulator 8. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be used including but not limited to tools with or without end effectors 120, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

In one example, (FIGS. 2A-2B) instrument 100 includes strain gauges mounted onto the exterior surface of force transducer 140 oriented parallel to the longitudinal (lengthwise) axis of the instrument shaft, termed the z-axis. The two axes perpendicular to the shaft are called the x- and y-axes. The signals from the strain gauges are combined arithmetically in various sums and differences to obtain measures of transverse forces Fx and Fy exerted upon the instrument tip while rejecting axial force Fz and torques Tx and Ty about the two axes perpendicular to the shaft axis. Forces exerted against end portion 120 are detected by the force sensing elements, which may be operably coupled to servo control via an interrogator 170 and a processor 180 for transmitting these forces to master(s). Examples of instruments including strain gauges and methods of force sensing are disclosed in U.S. patent application Ser. No. 11/537,241 filed on Sep. 29, 2006, and U.S. application Ser. No. 11/553,303 filed on Oct. 26, 2006, the full disclosures of which are incorporated by reference herein for all purposes.

In one example, various strain gauges 102 may be used, including but not limited to optic fiber type gauges using Bragg grating or Fabry-Perot technology. Optic fiber Bragg grating (FBG) gauges may be advantageous in that two sensing elements may be located along a single fiber 106 at a known separation L, thereby only requiring the provision of four fibers along the force transducer 140 and the instrument shaft 110 to connect eight strain gauges 102. Multiple FBGs can be written into a fiber if they are formed in such a way as to use different ranges of wavelengths. This is a particularly useful property for an embodiment comprising a pair of rings 104 of strain gauges because only four fibers would need to be passed thru the instrument shaft, each with two FBGs separated by a known distance L.

In the disclosures referenced above, a force transducer mounted to the distal end of an endoscopic surgical instrument shaft is described. In one embodiment, the force sensor comprises two groups (rings) of four strain gauges located about the periphery of the sensor such that the members of a group of four are situated in diametrically opposite pairs that are 90 degrees or other alternating supplementary angle pairs (e.g. 70 and 110 degrees) apart around the shaft and such that the two groups or rings of four are a distance L apart along the shaft. In one aspect, it is desired to determine the side load (e.g., Fy) on the instrument tip or jaws. By computing the bending moment due to the jaw side load at each group of four strain gauges based on the difference of strains on diametrically opposite strain gauge pairs and then subtracting the moment values at the two groups, a measure of the side load independent of wrist orientation and resulting effective lever arm length can be derived. Similarly, moments applied to the wrist clevis 160 and the distal end of the force transducer by the actuation of the instrument wrist axes and transmitted to the wrist clevis by the friction in the wrist pivots are felt equally at each group of four gauges and are thus eliminated by subtracting the moments measured at the two groups. Strains due to z-axis forces such as wrist actuator cable forces affect all strain gauges equally and are thus also eliminated by subtracting the signals from the two groups of four gauges.

Referring now to FIG. 2B, Fabry-Perot or FBG sensing elements 102 and fibers 106 may be embedded in shallow grooves below the force transducer 140 surface near the instrument shaft 110 distal end proximal to the wrist clevis 160 and end portion 120, and then epoxied or otherwise potted into place.

Referring again to FIG. 2A, a perspective view of instrument 100 including an optic fiber connector 300a mounted in housing 150 is illustrated in accordance with an embodiment of the present invention. In this embodiment, a plurality of strain gauges (e.g., strain gauges 102) embedded in a force transducer 140 at the distal end of shaft 110 are coupled to an optic fiber splitter 306 by an optic fiber ribbon cable 302 passing thru shaft 110. The optic fiber splitter 306 is coupled to optic fiber connector 300a by an optic fiber 326 that is routed through housing 150 in an L-shaped path, in one example. Optic fiber connector 300a is optically linkable with an optic fiber connector 300b (see also FIG. 13B) incorporated into the instrument mechanical interface of a distal link 66 (see, e.g., FIG. 11) such that installation of instrument 100 onto a manipulator 8 automatically forms an optical link with the instrument and signals from the instrument strain gauges related to force applied to the instrument tip may be passed to an interrogator 170 and processor 180. Advantageously, the present invention avoids the need to carry external cabling to the instrument.

Referring now to FIGS. 3A-3B, two different styles of fiber optic splitters are illustrated. FIG. 3A illustrates a fiber optic splitter 306 which is a 1×4 planar lightwave circuit (PLC) splitter. Light entering waveguides 318a-318d embedded in a silica body 316 at a first end of the silica body 316 is combined to exit at a second end of the silica body 316, or alternatively light entering at the second end through waveguide 318e is split equally among the four waveguides 318a-318d to exit through the first end of the silica body.

FIG. 3B shows another fiber optic splitter which may be used in embodiments of the present invention. A fused biconic taper (FBT) splitter 320 is illustrated in which four fibers 326 are twisted together along a zone "C" at high temperature until their cores are close enough to cause coupling of light among the cores with a result similar to the PLC splitter discussed above. Three of the four fibers at one end are terminated to create a 1×4 splitter.

Referring now to FIGS. 4A-4B, longitudinal cross-section views are illustrated of lensed optical fibers 322a and 322b, which are components of some embodiments of the present invention. A lensed fiber 322a or 322b includes a small (e.g., 0.5 mm) ball lens 312 integrated with an end of a fiber 326 either by bonding (FIG. 4A) or by fusing (FIG. 4B). Light emerging from a fiber core 328 diverges along a light ray path 330 and is then focused by the ball lens 312 resulting in collimated light 332 exiting the ball lens. Conversely, collimated light entering the ball lens and aligned with the fiber core axis is focused on the core end and then conducted along the core. The lensed fiber 322a or 322b may be used as the optical component of an expanded beam connector.

Referring now to FIG. 5, an aspheric lens fiber collimator 336, which may be used as the optical component of an expanded beam connector, is illustrated. Fiber collimator 336 includes an optic fiber 326, a housing 331, and an aspheric lens 334. Light emerging from a core of the optic fiber 326 diverges along a light ray path 330 within housing 331 and is then focused by aspheric lens 334, resulting in collimated light 332 exiting the aspheric lens 334. Conversely, collimated light entering lens 334 in alignment with the optical axis will be focused on the core of fiber 326 and conducted along the core.

FIGS. 6A1-6A2 and 6B1-6B2 illustrate embodiments of a close coupled or integrated collimating lens and a PLC splitter assembly. FIGS. 6A1-6A2 show a perspective view and a partial cutaway perspective view of a gradient index (GRIN) lens PLC splitter assembly 338 while FIGS. 6B1-6B2 show a perspective view and a partial cutaway perspective view of a ball lens PLC splitter assembly 340.

GRIN lens PLC splitter assembly 338 includes a fiber array block (FAB) 304 operably coupled to a PLC fiber optic splitter 306, which is operably coupled to a GRIN lens 308.

Ball lens PLC splitter assembly 340 includes a fiber array block (FAB) 304 operably coupled to a PLC fiber optic splitter 306, which is operably coupled to a ball lens 312.

In each case, collimated light entering the lens (lens 308 or 312) aligned with the optical axis is focused on the entrance to the PLC fiber optic splitter 306 and then split equally among the four other waveguides where the FAB 304 aligns four fibers so that their cores receive the light. Both devices 338 and 340 also operate in the reverse direction where the fibers of a 4-wide fiber ribbon cable 302 are aligned by the FAB 304 so that light conducted through the ribbon cable 302 enters the four waveguides and is combined through splitter 306 to then emerge as a collimated beam from the lens (lens 308 or 312). In each case the device may be used as the optical component of an expanded beam connector on the ribbon cable side of the connection.

FIGS. 7A-7B show views of an instrument including a fiber optic force transducer 140 similar to that described above with respect to FIGS. 2A-2B. Similar elements are numbered the same and repetitive descriptions are omitted to avoid redundancy. In this embodiment, the instrument has four fibers emerging from the transducer 140 which are gathered directly into PLC splitter 306 (integrated with the transducer) so that a single fiber 326 passes through the instrument shaft 110 to the rear housing 150 and expanded beam connector 300a. The fiber strain relief is in the form of a circular loop 326a and the optical connector 300a is oriented to the rear for manual mating with an optical connector 300b.

Figure 8A:
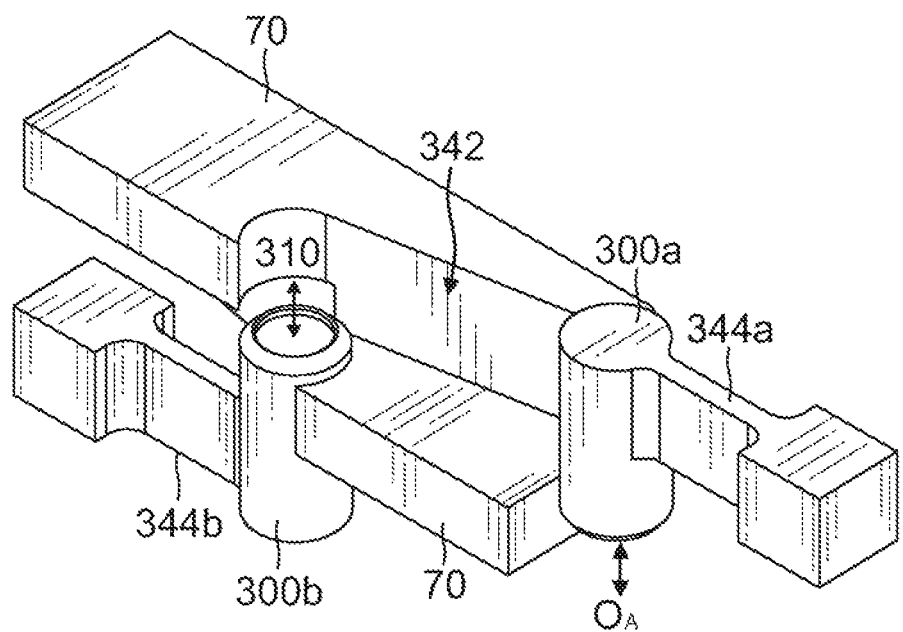
FIGS. 8A, 8B, and BC show different views of a tapered slot feature of an instrument sterile adaptor guiding and aligning a pair of flexibly mounted lensed fiber optic connectors.
Figure 8B:
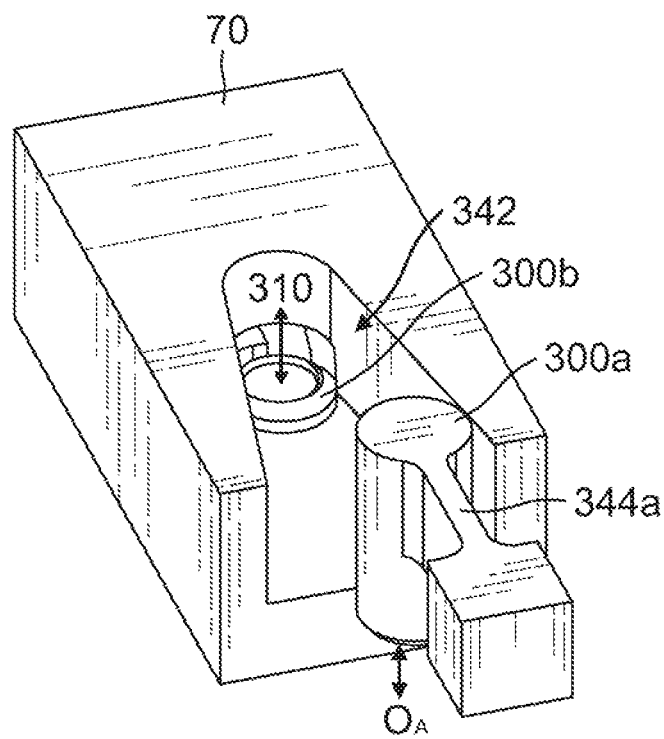
Figure 8C:
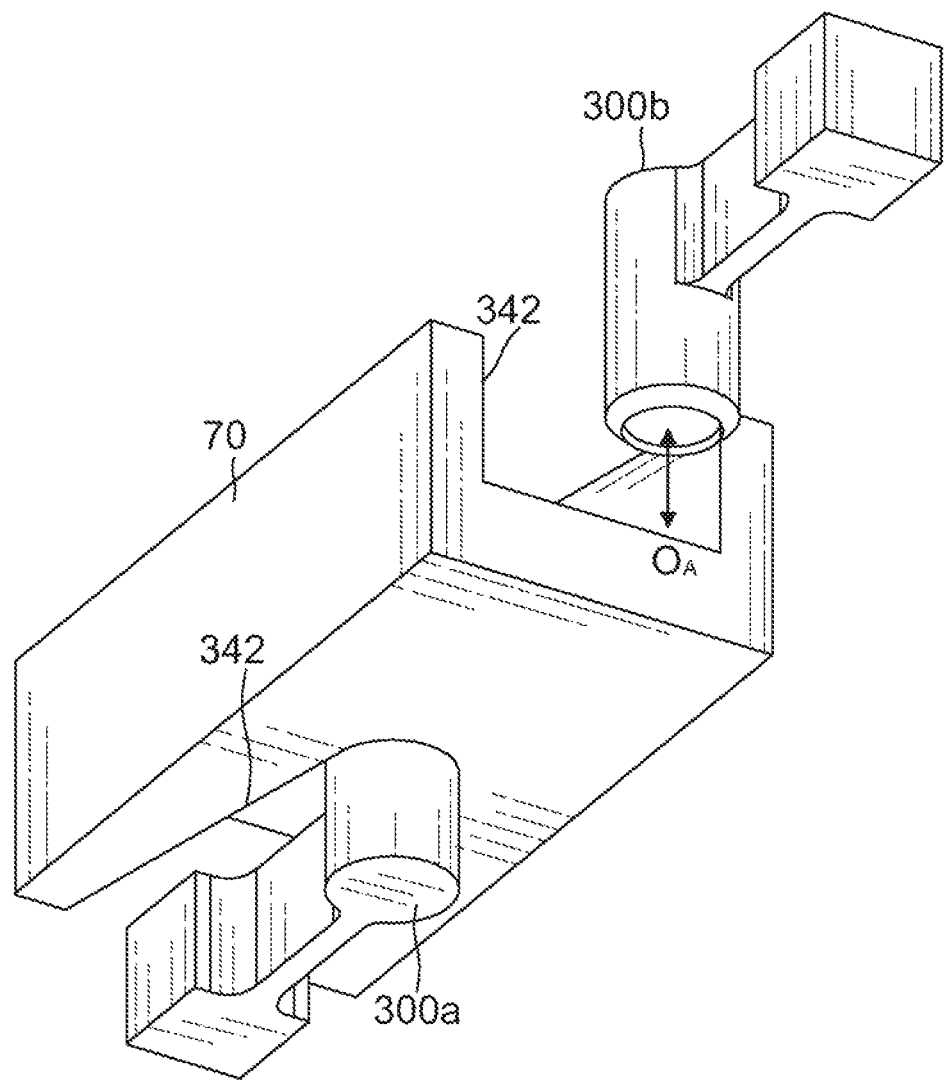

Referring now to FIGS. 8A-8C, different views are illustrated of a pair of back-to-back planar tapered features 342 of an instrument sterile adaptor (ISA) 70 which guide and align flexure mounted expanded beam connectors (EBC) (or more generally optical connectors) 300a, 300b on the manipulator (e.g., distal link 66 or instrument interface 61) and on the instrument housing with an optical path 310 through the ISA 70. FIG. 8A shows a perspective cross-sectional view of ISA 70, FIG. 8B shows a top perspective view, and FIG. 8C shows a bottom perspective view. This design of ISA 70 applies to the case of an instrument mounting motion which is transverse to the optical axis $O_A$ of the connectors 300a, 300b.

Figure 9A:
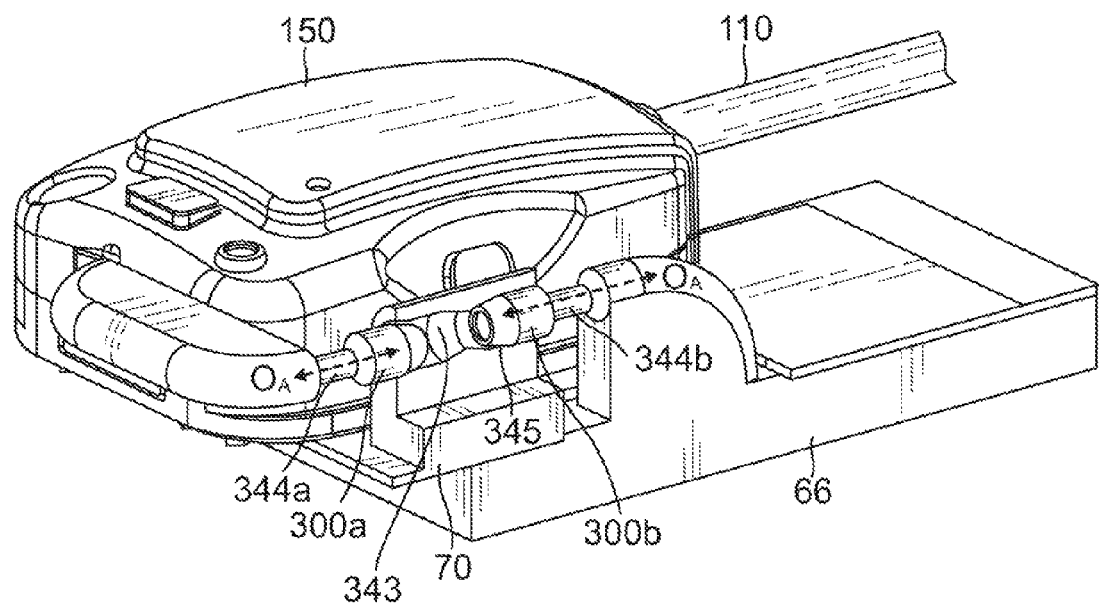
FIGS. 9A, 9B, and 9C show different views of a conically tapered feature of an instrument sterile adaptor guiding and aligning a pair of flexibly mounted lensed fiber optic connectors.
Figure 9B:
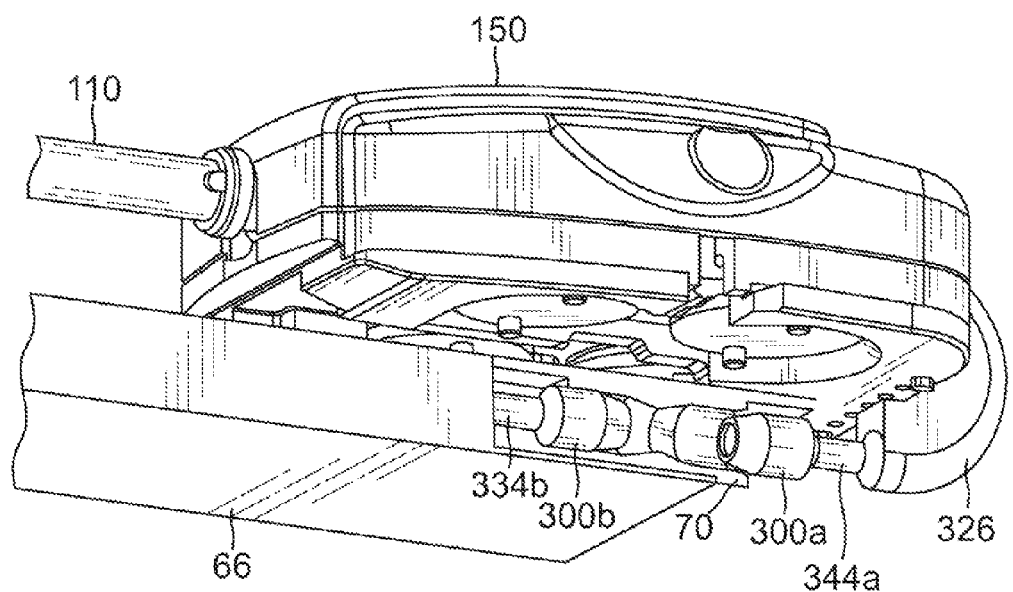
Figure 9C:
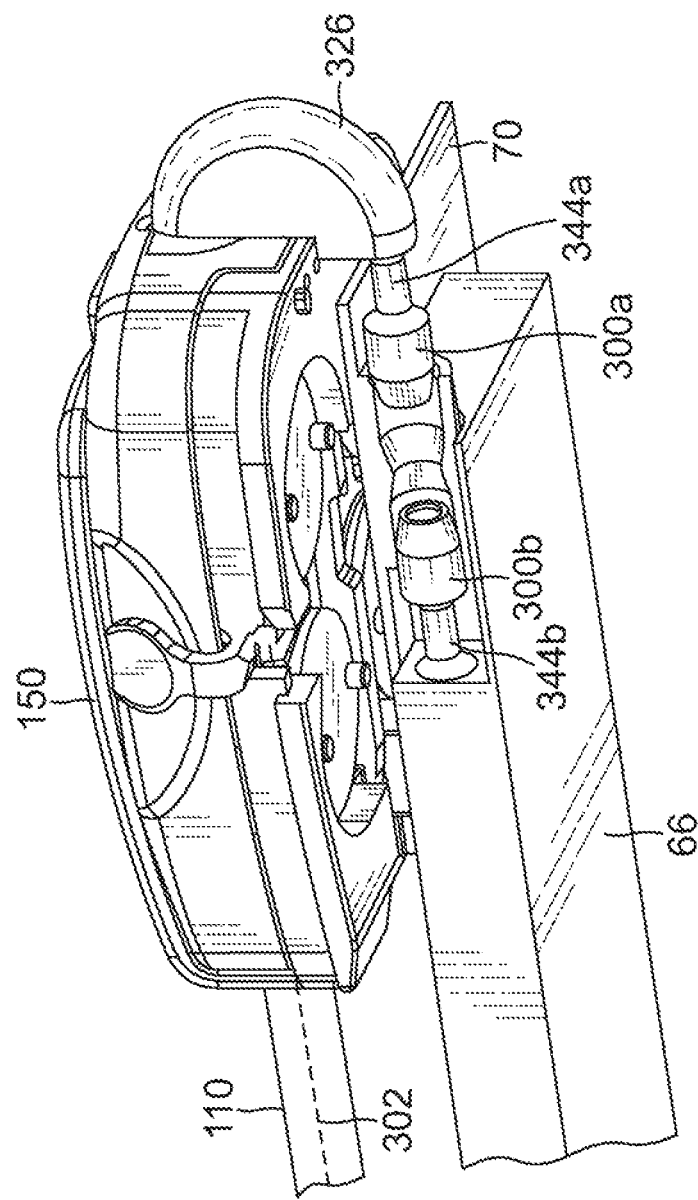

Referring now to FIGS. 9A-9C, flexure mounted EBCs on distal link 66 (EBC 300b) and the instrument housing 150 (EBC 300a) are shown to be guided and aligned by conically tapered features 343 of the sterile adaptor 70 and conically tapered features 345 of the EBCs. Conically tapered features 343 are provided as a canal through which conically tapered features 345 of the EBCs may be received to guide and align the optical axes $O_A$ of the EBCs 300a and 300b. This design applies to the case when the instrument mounting motion is parallel with the optical axis $O_A$ of the connectors.

FIGS. 10A-10D show orthographic views of an instrument rear housing including a fiber optic ribbon cable, a PLC fiber optic splitter, a strain relief loop of optical fiber or ribbon cable and an expanded beam optic fiber connector in accordance with embodiments of the present invention. Various advantageous features of the optics in the rear housing are shown.

FIG. 10A illustrates a U-shaped strain relieving "loop" of fiber (ribbon or single) to accommodate mechanical tolerances, ease assembly, and allow for thermal expansion during autoclaving. FIG. 10A further illustrates an optical connector including an aspheric lens 334 and a splitter 306 integrated within the optical connector.

FIGS. 10B and 10C similarly illustrate an L-shaped strain relieving loop of fiber (ribbon or single) to achieve similar advantages. It is noted that a strain relief loop of optical fiber or ribbon cable may bend 90 degrees, 180 degrees, or 360 degrees in one example. FIGS. 10B and 10C further illustrate a splitter 306 integrated within housing 150 and an optical connector including a lensed optical fiber 322 and a ball lens 312, respectively.

Finally FIG. 10D illustrates a strain relief loop of fiber (ribbon or single) to achieve similar advantages, and a GRIN lens PLC splitter assembly 338 at the rear of housing 150 allowing for manual mating, assembly 338 including a PLC fiber optic splitter 306 operably coupled to a GRIN lens 308.

Figure 11:
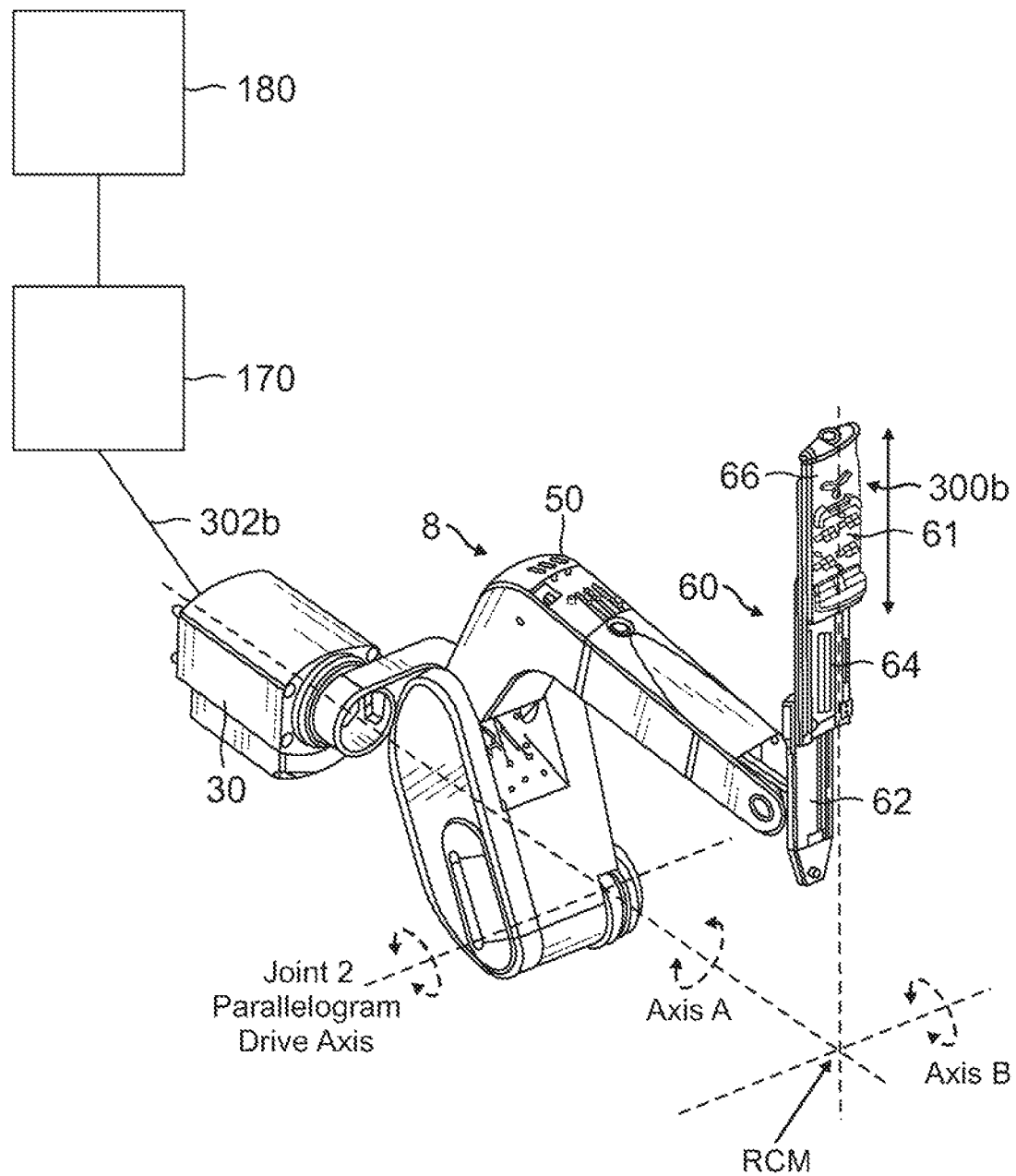
FIG. 11 is a perspective view of a surgical robotic manipulator including an optic fiber connector at an instrument interface of the distal link of the manipulator, the manipulator coupled to a fiber optic strain interrogator and a controller, in accordance with an embodiment of the present invention.

Referring now to FIGS. 11-13B, perspective views and respective perspective cross-sectional side views of a manipulator 8 including a manipulator arm link 50, a telescopic insertion axis 60, and an optic fiber connector 300b are shown in accordance with an embodiment of the present invention. In FIG. 11, an interrogator 170 is operably coupled to optic fiber connector 300b, and a computer 180 is optionally coupled to interrogator 170. The optic fiber technologies require an interrogator unit that decodes the optically encoded strain information from the instrument strain gauges into electrical signals compatible with the computer control hardware of the robotic surgical system. A processor (e.g., processor 4 of FIG. 1) may then be used to calculate forces according to equations in conjunction with the signals from the strain gauges/sensors. In one embodiment, interrogator 170 and computer 180 is mounted on the manipulator, at the system main chassis, or on an equipment rack elsewhere in the surgical system, which may require routing of the optical fiber across the sterile boundary.

Communication between optic fiber connector 300b and interrogator 170 may be accomplished through a noise immune cable, such as a fiber optic cable 302b, which is routed at least partially through manipulator arm 8 in one example. Interrogator 170 may communicate with computer 180 through various means, including but not limited to a serial input/output. In one example, computer 180 may output raw strain gauge data and/or resolved force/torque data in various formats, including but not limited to hexadecimal and decimal integer formats.

Figure 13A:
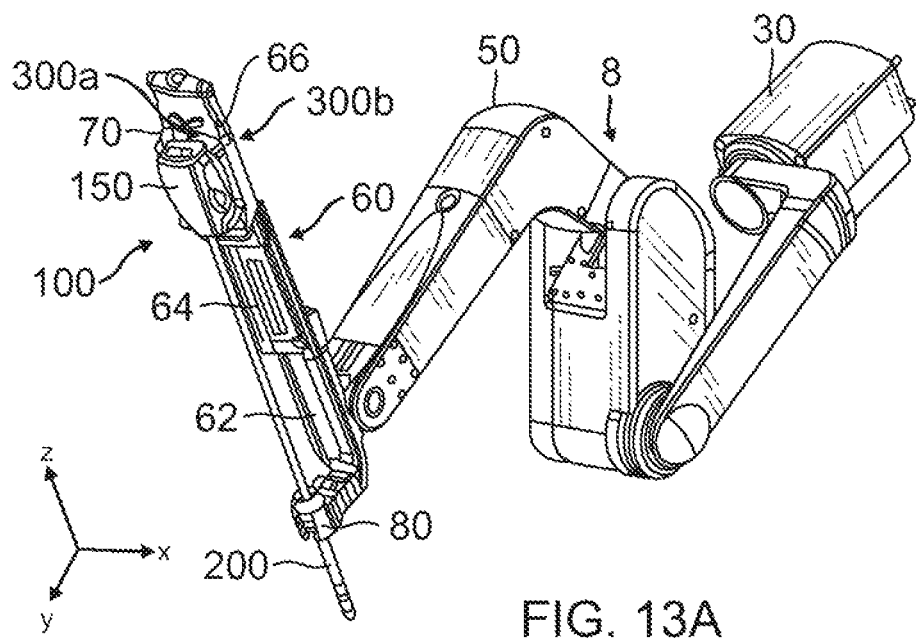
FIG. 13A is a perspective view of the manipulator of FIG. 12A, including the coupling of an instrument having a mating optic fiber connector, in accordance with an embodiment of the present invention.
Figure 13B:
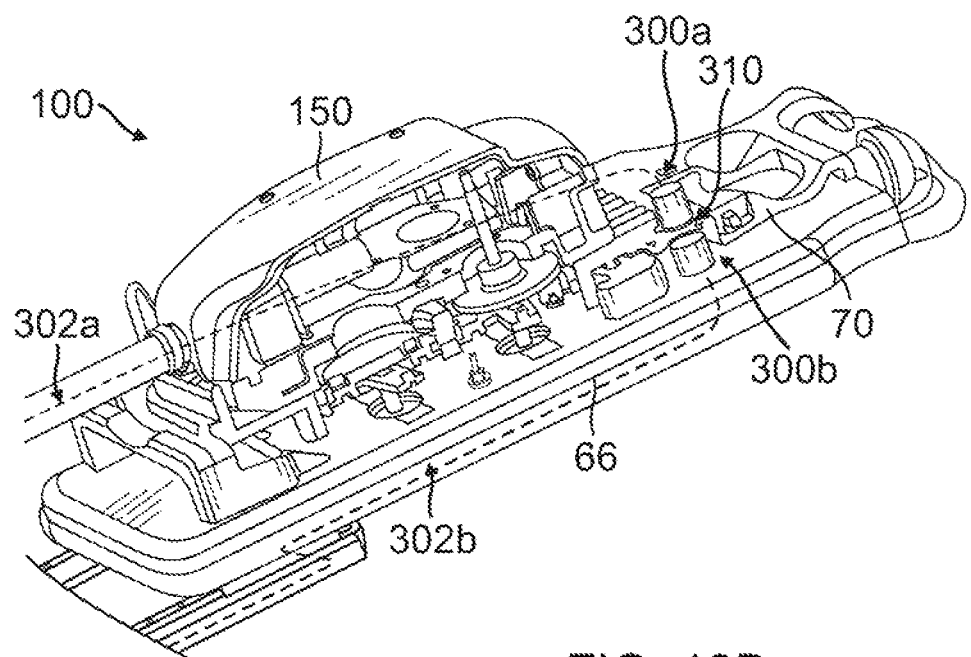
FIG. 13B is an enlarged sectional view of the instrument mounted to the sterile adaptor mounted to the distal link in accordance with an embodiment of the present invention.

Referring now to FIGS. 12A-12C and 13A-13B in conjunction with FIG. 11, the optic fiber connector 300b is shown to be incorporated on an instrument interface 61 of a distal link 66 of the manipulator and optic fiber cable 302b is routed at least partially through the manipulator linkage. FIG. 12A-12C illustrates the coupling of instrument sterile adaptor (ISA) 70 onto instrument interface 61 of distal link 66. FIGS. 13A and 13B illustrate the mounting of instrument 100 on ISA 70 and the optical link between optic fiber connectors 300a and 300b through ISA 70.

In one embodiment, telescopic insertion axis 60 includes a first link 62, a second link or idler link 64 operably coupled to link 62, and a third link or distal link 66 operably coupled to idler link 64. Some of the manipulators 8 include a telescopic insertion axis 60, although in other embodiments, the manipulators may include a linear sliding carriage as is described in greater detail in pending U.S. application Ser. No. 11/613,800, filed Dec. 20, 2006, which is incorporated by reference herein for all purposes. In yet other embodiments, the linear insertion motion of an attached instrument may result from the coordinated motion of multiple hinged or revolute joint links.

Distal link 66 includes an instrument interface 61 (FIG. 11) for operably coupling (electrically and/or physically) to ISA 70 (FIGS. 12A-12C), which is configured to operably couple (electrically and/or physically) to a housing of an instrument having an optic fiber connector 300a (e.g., housing 150 of FIGS. 13A and 14B). Optic fiber connector 300b is incorporated in instrument interface 61 to optically link with optic fiber connector 300a of a mounted instrument through ISA 70. As shown in FIG. 12B, ISA 70 includes an optical path in the form of an aperture 310 or a lens through which optic fiber connector 300b is optically linkable to optic fiber connector 300a (FIG. 13B) when the instrument is fully mounted on ISA 70. In one embodiment, the sterile adaptor is integrated with a drape that may be draped over the robotic surgical system, and in particular the manipulator system, to establish a sterile barrier between the non-sterile manipulator arms and the sterile field of the surgical procedure.

An example of applicable sterile adaptors and instrument housings are disclosed in U.S. application Ser. No. 11/314,040, filed Dec. 20, 2005 and in U.S. application Ser. No. 11/395,418, filed Mar. 31, 2006, the full disclosures of which are incorporated by reference herein for all purposes. An example of an applicable drape and adaptor is disclosed in pending U.S. application Ser. No. 11/240,113, filed Sep. 30, 2005, the full disclosure of which is incorporated by reference herein for all purposes. An example of an instrument interface is disclosed in pending U.S. application Ser. No. 11/613,695, filed Dec. 20, 2006, the full disclosure of which is incorporated by reference herein for all purposes.

It is noted that the optical connectors 300a, 300b (such as EBCs) described above may include the various collimating lenses and assemblies described above with respect to FIGS. 4A-6B2 and may be mounted on respective flexure beams 344a, 344b. The optic fiber connectors may further include a fiber array block that receives a fiber ribbon cable, a planar lightwave circuit (PLC) splitter operably coupled to the fiber array block, and a collimator lens operably coupled to the PLC splitter. The PLC splitter advantageously provides a compact means for combining signals from fiber optic sensors into fewer or preferably one fiber and for separating signals on one or more fibers onto a larger number of fibers.

The respective collimator lens of the optic fiber connectors enables light to be transmitted between the optic fiber connectors with less sensitivity to contamination of the mating surfaces, misalignment, and gap sensitivity by spreading light over a larger area, which may be more easily cleaned with minimal training of operating room staff. Although light is spread over a larger area, the power level and spectral distribution of the light is preserved to prevent degradation of signals between the connectors. In one example, the collimator lens is formed of an aspheric lens, a GRIN lens, a ball lens, or a lensed fiber. In other embodiments, a plurality of lenses may be used.

Further, the PLC splitter may be mounted in the instrument housing and connected by a single fiber with the EBC (FIGS. 2A, 10B, 10C) or the PLC splitter may be integrated with (i.e. directly coupled to) the EBC (FIGS. 6A1, 6A2, 6B1, 6B2, 10A, 10D). In yet another embodiment the PLC splitter may not be mounted in the housing but may be integrated with the force transducer (FIG. 7A, 7B). The optic fiber connectors may also have their optical axis either aligned (FIGS. 9A-9C, 10A) or transverse (FIGS. 8A-8C, 10B, 10C) to the mating direction of the instrument with the sterile adaptor and of the EBC pair. Finally, manual mating of the EBC pair at the rear of the instrument housing may be provided (FIGS. 7A, 10D).

Alternatively, an optical multiplexer/demultiplexer (OMUX) chip can replace the PLC splitter between the fiber array block and the collimator lens. In one example, a planar arrayed waveguide grating (AWG) OMUX chip and its associated optic fiber connections can be used. Preferably, the AWG OMUX will be of the coarse wavelength division multiplexer (CWDM) type. Each channel of the device will have a wavelength pass band wide enough to accommodate the range of reflected wavelength variations from fiber optic strain sensors on the fiber entering that channel. The variations include those due to applied loads, temperature changes and also residual stress offsets from bonding the fibers to the force transducer. The channel bandwidth must also be sufficient to allow for temperature induced variations in the AWG OMUX channel center wavelength. The AWG OMUX chip is of an athermal temperature compensated type in a further example.

Advantageously, the present invention provides for reliable coupling of a force sensing instrument to a manipulator, such that the effect of optical surface contamination and optical axis misalignment are reduced while signal quality is maintained. Furthermore, the need for a long cable attached to the instrument is eliminated, thus removing or lessening potential problems with rapid instrument interchange, sterile draping and handling, and instrument re-sterilization between uses.

Embodiments described above illustrate but do not limit the invention. It should also be understood that numerous modifications and variations are possible in accordance with the principles of the present invention. Accordingly, the scope of the invention is defined only by the following claims.

We claim:

1. A method of making a surgical instrument comprising:
    coupling an optic splitter to a plurality of fiber optic stain gauges, the plurality of fiber optic strain gauges being coupled to a shaft of the surgical instrument; and
    coupling a fiber optic connector to the optic splitter, the fiber optic connector being configured for mounting in a housing of the surgical instrument.

2. The method of claim 1, wherein the fiber optic connector includes an expanded beam collimator lens.

3. The method of claim 1, the optic splitter comprising a fiber optic splitter, and the method further comprising routing optic fibers including the plurality of strain gauges at least partially through the shaft.

4. The method of claim 3, further comprising configuring the optic fibers in a loop at the housing.

5. The method of claim 1, further comprising configuring the fiber optic connector to transmit signals from the plurality of strain gauges to a second fiber optic connector mounted on a distal link of a manipulator arm.

6. The method of claim 1, wherein the optic splitter comprises an arrayed waveguide grating (AWG) multiplexer.

7. The method of claim 6, wherein the fiber optic connector comprises an expanded beam collimator lens, and wherein the method further comprises coupling the AWG multiplexer directly to the expanded beam collimator lens without optical fiber.

8. The method of claim 6, the method further comprising routing optic fibers including the plurality of strain gauges at least partially through the shaft to the AWG multiplexer.

9. The method of claim 8, further comprising configuring the optic fibers in a loop at the housing.

* * * * *